(12) United States Patent
Tanifum et al.

(10) Patent No.: US 11,779,664 B2
(45) Date of Patent: Oct. 10, 2023

(54) TARGETED CONTRAST AGENTS FOR MRI OF ALPHA-SYNUCLEIN DEPOSITION

(71) Applicants: Texas Children's Hospital, Houston, TX (US); Alzeca Biosciences, LLC, Houston, TX (US)

(72) Inventors: Eric A. Tanifum, Richmond, TX (US); Xianwei Sun, Houston, TX (US); Ananth V. Annapragada, Manvel, TX (US); Carlo Medici, Reno, NV (US)

(73) Assignees: Texas Children's Hospital, Houston, TX (US); Alzeca Biosciences, LLC, Houston, TX (US)

( * ) Notice: Subject to any disclaimer, the term of this patent is extended or adjusted under 35 U.S.C. 154(b) by 0 days.

(21) Appl. No.: 17/737,928

(22) Filed: May 5, 2022

(65) Prior Publication Data

US 2022/0265868 A1 Aug. 25, 2022

Related U.S. Application Data

(63) Continuation-in-part of application No. 17/175,359, filed on Feb. 12, 2021.
(Continued)

(51) Int. Cl.
*A61K 9/00* (2006.01)
*A61K 49/08* (2006.01)
(Continued)

(52) U.S. Cl.
CPC .......... *A61K 49/085* (2013.01); *A61K 9/1271* (2013.01); *A61K 47/542* (2017.08);
(Continued)

(58) Field of Classification Search
CPC .................................................. A61K 49/085
See application file for complete search history.

(56) References Cited

U.S. PATENT DOCUMENTS 9,744,251 B2 8/2017 Annapragada et al.
2013/0123367 A1 5/2013 Erker et al.

FOREIGN PATENT DOCUMENTS

WO 2012139080 10/2012

OTHER PUBLICATIONS

Kars, Development of Rational In Vitro Models for Drug Resistance in Breast Cancer and Modulation of MDR by Selected Compounds, Anticancer Research, 2006, 26, 4559-4568 (Year: 2006).*
(Continued)

*Primary Examiner* — Paul W Dickinson
(74) *Attorney, Agent, or Firm* — Benjamen E. Kern; Charlemagne Kern; Kern Kendrick, LLC

(57) ABSTRACT

A liposomal composition ("ADx-003") is provided, ADx-003 comprising a first phospholipid; a sterically bulky excipient that is capable of stabilizing the liposomal composition; a second phospholipid that is derivatized with a first polymer; a macrocyclic gadolinium-based imaging agent; and a third phospholipid that is derivatized with a second polymer, the second polymer being conjugated to a targeting ligand, the targeting ligand being represented by Formula I:

(Continued)

wherein X is —CH$_2$—, —CH$_2$—CH$_2$—, —CHO—, or —O—CO—; Y is —CH—CH═CH— or

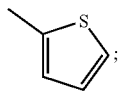

A and B are independently selected from C and N; $R_1$, $R_2$, $R_3$, and $R_4$ are independently selected from —H, halogen, —OH, and —CH$_3$; and $R_5$, $R_6$, and $R_7$ are independently selected from —H, halogen, —OH, —OCH$_3$, —NO$_2$, —N(CH$_3$)$_2$, $C_1$-$C_6$ alkyl, or a substituted or unsubstituted $C_4$-$C_6$ aryl group, except that when A and/or B is N the adjacent $R_5$ and/or $R_7$ is —H, or a pharmaceutically acceptable salt thereof.

11 Claims, 28 Drawing Sheets

Related U.S. Application Data

(60) Provisional application No. 63/184,675, filed on May 5, 2021, provisional application No. 62/975,265, filed on Feb. 12, 2020.

(51) Int. Cl.
| | |
|---|---|
| *C07C 49/755* | (2006.01) |
| *C07C 65/40* | (2006.01) |
| *C07D 333/22* | (2006.01) |
| *A61K 49/18* | (2006.01) |
| *A61K 47/54* | (2017.01) |
| *A61K 9/127* | (2006.01) |
| *A61K 49/10* | (2006.01) |

(52) U.S. Cl.
CPC .......... *A61K 47/544* (2017.08); *A61K 47/545* (2017.08); *A61K 49/108* (2013.01); *A61K 49/1812* (2013.01); *C07C 49/755* (2013.01); *C07C 65/40* (2013.01); *C07D 333/22* (2013.01)

(56) References Cited

OTHER PUBLICATIONS

International Search Report and Written Opinion issued in PCT/US2021/017986, dated Jun. 8, 2021.
PubChem-SID: 103922340 Deposit Date: Jan. 19, 2011, pp. 1-6; p. 2.

\* cited by examiner

Table 1

| Compd | ID | Abs_max | Em_max | Kd α-syn (nM) | Log P | Compd | ID | Abs_max | Em_max | Kd α-syn (nM) | Log P |
|---|---|---|---|---|---|---|---|---|---|---|---|
| 7 | XW-01-58 | 332 | 430 | NB | 4.9 | 32 | XW-01-64 | 352 | 596 | 18.8 ± 4.0 | 4.9 |
| 8 | XW-01-11 | 408 | 598 | 9.0 ± 0.5 | 3.5 | 33 | XW-02-07 | 398 | 565 | 148.7 ± 20.6 | 5.4 |
| 9 | XW-02-24 | 455 | 620 | 38.4 ± 1.3 | 4.0 | 34 | XW-01-63 | 358 | 409 | 1426.3 ± 46.8 | 4.4 |
| 10 | XW-01-09 | 336 | 438 | 335 ± 27.0 | 3.6 | 35 | XW-01-60 | 392 | 614 | 74.2 ± 14.3 | 4.4 |
| 11 | XW-01-52 | 335 | 429 | NB | 4.5 | 37 | XW-01-92 | 414 | 524 | 38.7 ± 4.1 | 4.6 |
| 12 | XW-01-61 | 406 | 614 | 202.9 ± 15.9 | 3.9 | 38 | XW-02-16 | 408 | 563 | 159.8 ± 10.0 | 4.4 |
| 13 | XW-01-16 | 356 | 443 | 726.0 ± 23.6 | 3.3 | 39 | XW-02-17 | 431 | 612 | 93.1 ± 13.8 | 4.1 |
| 14 | XW-01-18 | 338 | 545 | 240.6 ± 47.9 | 3.8 | 40 | XW-02-14 | 413 | 597 | 160.4 ± 7.1 | 5.5 |
| 15 | XW-01-17 | 330 | 439 | 398.1 ± 3.9 | 3.9 | 41 | XW-01-84 | 410 | 567 | 272.1 ± 29.9 | 4.1 |
| 16 | XW-01-53 | 331 | 421 | NB | 3.1 | 42 | XW-02-15 | 396 | 582 | 92.9 ± 6.3 | 4.3 |
| 17 | XW-01-50 | 328 | 419 | NB | 3.9 | 43 | XW-01-83 | 386 | 572 | 236.4 ± 10.4 | 3.7 |
| 18 | XW-01-01 | 332 | 421 | NB | 3.3 | 44 | XW-02-01 | 412 | 545 | 134.1 ± 19.2 | 4.3 |
| 19 | XW-01-05 | 416 | — | NB | 3.4 | 46 | XW-01-89 | 368 | 454 | 153.3 ± 7.9 | 4.6 |
| 20 | XW-01-02 | 448 | 583 | 44.5 ± 6.1 | 2.6 | 47 | XW-02-02 | 340 | 404 | 333.1 ± 28.3 | 3.8 |
| 21 | XW-01-56 | 434 | 450 | 268.2 ± 11.7 | 2.5 | 49 | XW-02-87 | 372 | 551 | 161.6 ± 13.6 | 5.1 |
| 22 | XW-01-03 | 336 | 460 | 1325.3 ± 181.8 | 2.8 | 50 | XW-02-88 | 417 | 596 | 110.7 ± 7.8 | 5.1 |
| 23 | XW-02-21 | 401 | 586 | 85.1 ± 13.4 | 3.9 | 51 | XW-02-89 | 442 | 613 | 106.9 ± 7.5 | 4.5 |
| 24 | XW-02-22 | 397 | 553 | 97.6 ± 5.7 | 4.7 | 52 | XW-01-29 | 354 | 406 | NB | 2.7 |
| 25 | XW-02-90 | 490 | 621 | 116.3 ± 0.7 | 2.9 | 53 | XW-01-28 | 428 | 471 | NB | 2.3 |
| 26 | XW-01-45 | 440 | 657 | 118.5 ± 21.1 | 3.7 | 54 | XW-01-27 | 336 | 409 | NB | 3.9 |
| 27 | XW-01-46 | 442 | 661 | 114.3 ± 13.5 | 4.2 | 55 | XW-01-31 | 384 | 519 | 1183.1 ± 447.4 | 2.2 |
| 28 | XW-01-47 | 405 | — | NB | 4.5 | 56 | XW-01-91 | 321 | 409 | NB | 3.8 |
| 29 | XW-02-20 | 397 | 551 | 66.7 ± 2.0 | 5.2 | 57 | XW-01-33 | 326 | 388 | 655.6 ± 88.0 | 2.8 |
| 30 | XW-02-13 | 414 | 597 | 236.3 ± 10.5 | 5.6 | 58 | XW-01-38 | 344 | 385 | 1685.3 ± 252.0 | 2.4 |
| 31 | XW-01-87 | 368 | 540 | 125.5 ± 5.0 | | | | | | | |

FIG. 12

Table 2

| Compound ID | Absorption | | Emission | | Fluorescence quantum yield | | |
|---|---|---|---|---|---|---|---|
| | Ligand + estr. | Ligand + alb. | Ligand + estr. | Ligand + alb. | Free ligand | Ligand + estr. | Ligand + alb. |
| 8 | XW-03-11 | 446 | 441 | 595 | 579 | 0.0079 | 0.078 | 0.1363 |
| 9 | XW-02-24 | 462 | 460 | 610 | 609 | 0.0059 | 0.0805 | 0.1465 |
| 20 | XW-01-02 | 440 | 435 | 603 | 596 | 0.0061 | 0.0482 | 0.1419 |
| 23 | XW-02-21 | 447 | 453 | 587 | 584 | 0.0051 | 0.0698 | 0.1690 |
| 24 | XW-03-22 | 452 | 434 | 582 | 585 | 0.0063 | 0.0766 | 0.1377 |
| 29 | XW-02-39 | 426 | 449 | 583 | 574 | 0.0052 | 0.1125 | 0.1543 |
| 32 | XW-01-44 | 446 | 437 | 586 | 583 | 0.0034 | 0.0878 | 0.2498 |
| 34 | XW-01-60 | 432 | 446 | 601 | 595 | 0.0097 | 0.0765 | 0.2038 |
| 37 | XW-03-92 | 443 | 448 | 553 | 538 | 0.0063 | 0.0835 | 0.0074 |
| 38 | XW-02-17 | 439 | 445 | 589 | 586 | 0.0031 | 0.0835 | 0.1577 |
| 42 | XW-03-13 | 465 | 476 | 572 | 581 | 0.0050 | 0.0596 | 0.1130 |

FIG. 14

Table 3

| Comp # | ID | K-a-syn (nM) | K-Aβ (nM) | Selectivity (Aβ vs a-syn) |
|---|---|---|---|---|
| 8 | XW-01-11 | 9.7 ± 0.6 | 140.3 ± 4.2 | 14.4 |
| 9 | XW-02-24 | 30.2 ± 4.0 | 156.7 ± 5.0 | 5.2 |
| 20 | XW-01-02 | 38.5 ± 0.9 | 154.1 ± 11.8 | 4.0 |
| 23 | XW-02-21 | 76.1 ± 23.4 | 143.7 ± 13.0 | 1.8 |
| 26 | XW-02-22 | 94.8 ± 6.3 | 165.2 ± 7.1 | 1.7 |
| 29 | XW-02-30 | 70.4 ± 9.6 | 52.5 ± 3.1 | 0.7 |
| 32 | XW-01-44 | 18.8 ± 4.5 | 491.1 ± 58.9 | 26 |
| 34 | XW-01-60 | 87.6 ± 16.8 | 337.3 ± 11.7 | 3.8 |
| 37 | XW-01-92 | 34.9 ± 2.6 | 392.5 ± 64.4 | 11.2 |
| 39 | XW-02-17 | 60.1 ± 32.9 | 256.7 ± 20.3 | 4.2 |
| 42 | XW-02-15 | 91.2 ± 4.3 | 250.0 ± 37.1 | 2.7 |

FIG. 15

TARGETED CONTRAST AGENTS FOR MRI OF ALPHA-SYNUCLEIN DEPOSITION

CROSS-REFERENCE TO RELATED APPLICATIONS

This application is a continuation in part of U.S. patent application Ser. No. 17/175,359, filed on Feb. 12, 2021, which claims the benefit of U.S. Provisional Patent Application No. 62/975,265, filed on Feb. 12, 2020. This application also claims the benefit of U.S. Provisional Patent Application No. 63/184,675, filed on May 5, 2021. Each of these applications is incorporated by reference herein in its entirety.

BACKGROUND

Neurodegenerative disorders such as Parkinson's disease ("PD") and Alzheimer's disease ("AD") are characterized by pathological deposits of misfolded protein aggregates at different locations in the brain. These misfolded protein aggregates include alpha-synuclein ("α-syn") aggregates in the form of Lewy bodies ("LB") and Lewy neurites ("LN") in PD and amyloid-beta ("Aβ") plaques and hyperphosphorylated tau tangles in AD. PD is the second most common neurodegenerative disease after AD and is characterized clinically by motor symptoms, including bradykinesia, rigidity, tremor, and postural instability. The motor symptoms are caused by degeneration of dopaminergic neurons in the substantia nigra, accompanied by cytoplasmic deposition of Lewy pathology. Regional distribution of α-syn in PD postmortem studies suggests that Lewy pathology originates from the olfactory bulb and the lower brain stem and progressively spreads to other areas of the central nervous system. High levels of LB and LN are observed in the medulla oblongata/pontine tegmentum and anterior olfactory structures (Braak Stages 1 and 2) prior to patient manifestation of any PD-related motor symptoms. PD-related motor symptoms only begin manifesting at the intermediate stages (Braak stages 3 and 4), when the pathology has spread to the substantia nigra and other nuclei within the basal portions of the mid- and forebrain. Apart from PD, the pathogenesis of several other neurodegenerative disorders (collectively referred to as "synucleinopathies"), including PD dementia ("PDD"), dementia with LB ("DLB"), multiple system atrophy ("MSA"), and pure autonomic failure ("PAF"), are also characterized by misfolded α-syn aggregates.

The correlation between Lewy pathology from autopsy studies with nigrostriatal degeneration, cognitive impairment, and motor dysfunction, suggests that technologies that can enable noninvasive detection and quantification of α-syn aggregates are invaluable tools for early diagnosis and clinical evaluation of LB disorders in living individuals. Early detection can provide better opportunities for recruitment of enriched patient cohorts for clinical trials, evaluation of disease reversing therapies, and validation of therapeutic efficacy of new drug candidates.

However, a further complication exists, in that LB disorders often present multiple proteinopathies. For instance, a study focused on PD patients who developed dementia revealed that apart from α-syn accumulation in the neocortex, widespread Aβ accumulation also presented in about 60% of the patients. In addition, about 3% of the cases showed tau accumulation along with α-syn and Aβ.

The recent approval of several Aβ positron emission tomography ("PET") imaging agents has greatly improved the enrichment of cohorts for AD drug clinical trials. This has also invigorated the search for similar agents for the other proteinopathies—tau- and synucleinopathies. A variety of molecular scaffolds (FIG. 1) with moderate to high binding affinity to α-syn fibrils have been reported over the past decade, but none have been successful in clinical translation, at least in part due to low selectivity for α-syn versus Aβ fibrils. Thus, a need exists for diverse molecular scaffolds with high affinity and selectivity for α-syn fibrils for in vitro screening assays.

Further, if such scaffolds were suitable for use with magnetic resonance imaging ("MRI"), the results could be transformative due to ease of accessibility and low cost (compared to PET). Recently, high T1 relaxivity, liposomal-gadolinium (Gd) nanoparticle contrast agents (containing a highly stable, macrocyclic gadolinium-based imaging agent comprising gadolinium(3+) 2-[4,7,10-tris(carboxylatomethyl)-1,4,7,10-tetrazacyclododec-1-yl]acetate ("gadoterate" or "Gd(III)-DOTA"), conjugated to a phospholipid and to the internal and external surfaces of the liposome bilayer) have enabled in vivo MRI of amyloid plaques (see U.S. Pat. No. 11,116,854), of tau pathology (see WO2021007232A1), and of α-syn pathology (see WO2020154623A1) (each of these applications is incorporated by reference herein in its entirety). Nonetheless, an urgent need remains for additional stable, targeted liposomal Gd contrast agents for MRI of α-syn deposits.

SUMMARY

In one aspect, a liposomal composition ("ADx-003") is provided, ADx-003 comprising a first phospholipid; a sterically bulky excipient that is capable of stabilizing the liposomal composition; a second phospholipid that is derivatized with a first polymer; a macrocyclic gadolinium-based imaging agent; and a third phospholipid that is derivatized with a second polymer, the second polymer being conjugated to a targeting ligand, the targeting ligand being represented by Formula I:

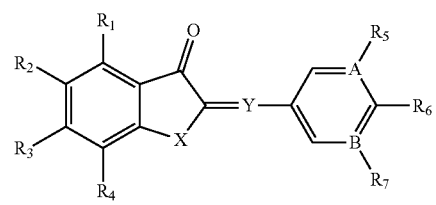

wherein X is —$CH_2$—, —$CH_2$—$CH_2$—, —CHO—, or —O—CO—; Y is —CH—CH═CH— or

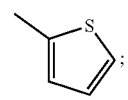

A and B are independently selected from C and N; $R_1$, $R_2$, $R_3$, and $R_4$ are independently selected from —H, halogen, —OH, and —$CH_3$; and $R_5$, $R_6$, and $R_7$ are independently selected from —H, halogen, —OH, —$OCH_3$, —$NO_2$, —$N(CH_3)_2$, $C_1$-$C_6$ alkyl, or a substituted or unsubstituted $C_4$-$C_6$ aryl group, except that when A and/or B is N the adjacent $R_5$ and/or $R_7$ is —H, or a pharmaceutically acceptable salt thereof.

In a further aspect, the first phospholipid comprises hydrogenated soy L-α-phosphatidylcholine ("HSPC"); the sterically bulky excipient that is capable of stabilizing the liposomal composition comprises cholesterol ("Chol"); the second phospholipid that is derivatized with a first polymer comprises 1,2-distearoyl-sn-glycero-3-phosphoethanolamine-N-(methoxy (polyethylene glycol)-2000) ("DSPE-mPEG2000"); and the macrocyclic gadolinium-based imaging agent comprises Gd(III)-DOTA and is conjugated to a fourth phospholipid, e.g.:

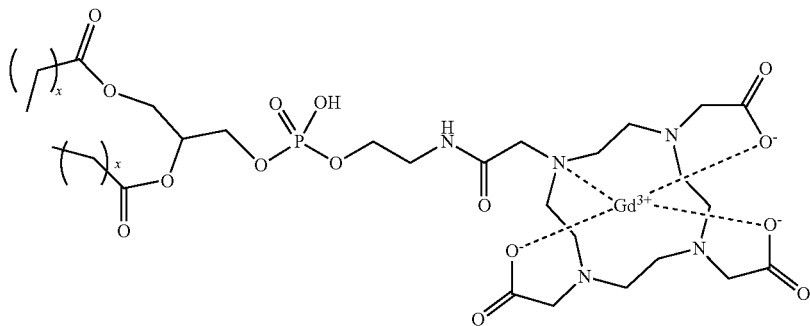

or a salt (e.g., a sodium salt) thereof. In some aspects, the variable x may be one of: 12, 13, 14, 15, 16, 17, or 18. In one aspect, the variable x is 16 (the conjugate: "Gd(III)-DOTA-DSPE").

In some aspects, the third phospholipid that is derivatized with a second polymer, the second polymer being conjugated to the targeting ligand, may comprise:

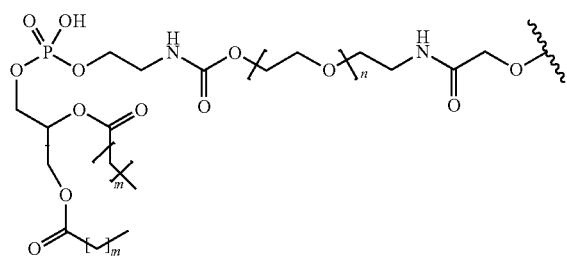

or a salt (e.g., an ammonium phosphate salt) thereof. In some aspects, the variable n may be any integer from about 10 to about 100, for example, about 60 to about 100, about 70 to about 90, about 75 to about 85, about 77, or about 79. The variable m may be one of: 12, 13, 14, 15, 16, 17, or 18. For example, n may be 77, and m may be 14; n may be 79, and m may be 14; n may be 77, and m may be 16; and n may be 79, and m may be 16.

In one aspect, the targeting ligand aspect of the phospholipid-polymer-targeting ligand conjugate comprises:

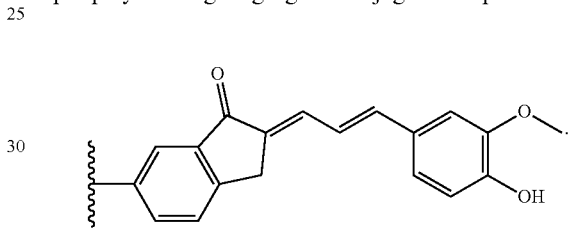

In one aspect, n is 77, m is 16 ("DSPE-PEG3400"), and the phospholipid-polymer-targeting ligand conjugate comprises:

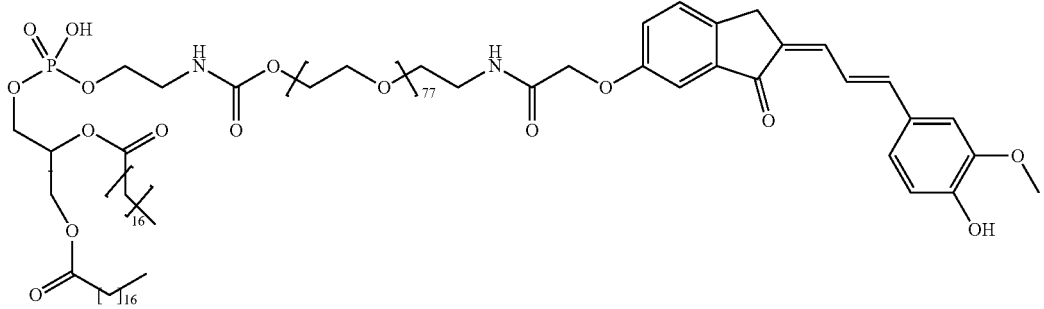

(the "DSPE-PEG3400-XW-01-11 Conjugate").

Alternatively, n is 79, m is 16 ("DSPE-PEG3500"), and the phospholipid-polymer-targeting ligand conjugate comprises:

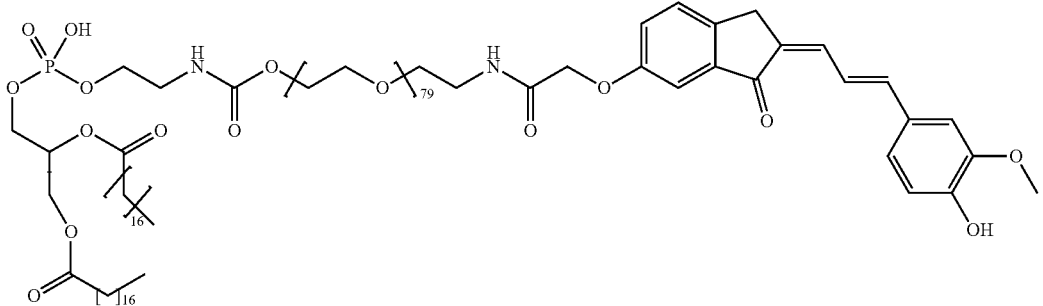

(the "DSPE-PEG3500-XW-01-11 Conjugate").

In one aspect, a method for imaging α-syn deposits in a subject is provided. The method may comprise introducing into the subject a detectable quantity of liposomal composition. The method may comprise allowing sufficient time for the liposomal composition to be associated with one or more α-syn deposits. The method may comprise detecting the liposomal composition associated with the one or more α-syn deposits.

In one aspect, the liposomal composition of the method for imaging α-syn deposits in a subject may comprise ADx-003. In one aspect, the liposomal composition of the method for imaging α-syn deposits in a subject may comprise Gd(III)-DOTA-DSPE and the DSPE-PEG3400-XW-01-11 Conjugate or the DSPE-PEG3500-XW-01-11 Conjugate. In one aspect, the liposomal composition of the method for imaging α-syn deposits in a subject may comprise HSPC, Chol, DSPE-mPEG2000, Gd(III)-DOTA-DSPE, and the DSPE-PEG3400-XW-01-11 Conjugate or the DSPE-PEG3500-XW-01-11 Conjugate.

In one aspect, the liposomal compositions are suitable for use in imaging α-syn deposits in a patient, the use comprising: introducing into the patient a detectable quantity of the liposomal composition; allowing sufficient time for the liposomal composition to be associated with one or more α-syn deposits; and detecting the liposomal composition associated with the one or more α-syn deposits. In one aspect, the detecting comprises detecting using MRI.

In one aspect, the use further comprises identifying the patient as having PD according to detecting the liposomal composition associated with the one or more α-syn deposits.

In one aspect, a phospholipid-polymer-targeting ligand conjugate is provided, the phospholipid-polymer aspect of the phospholipid-polymer-targeting ligand conjugate comprising:

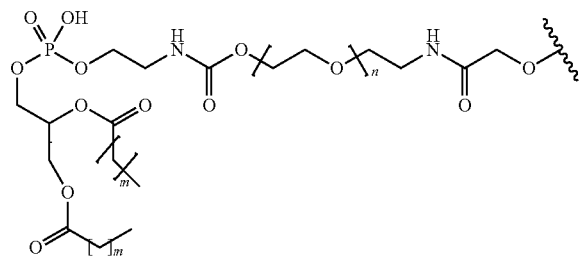

or a salt (e.g., an ammonium phosphate salt) thereof. In some aspects, the variable n may be any integer from about 10 to about 100, for example, about 60 to about 100, about 70 to about 90, about 75 to about 85, about 77, or about 79. The variable m may be one of: 12, 13, 14, 15, 16, 17, or 18. For example, n may be 77, and m may be 14; n may be 79, and m may be 14; n may be 77, and m may be 16; and n may be 79, and m may be 16.

In one aspect, the targeting ligand aspect of the phospholipid-polymer-targeting ligand conjugate is represented by:

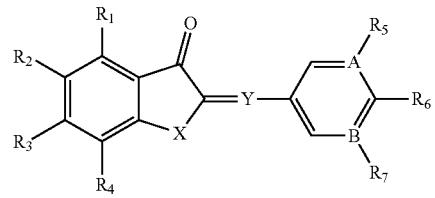

wherein X is —CH$_2$—, —CH$_2$—CH$_2$—, —CHO—, or —O—CO—; Y is —CH—CH=CH— or

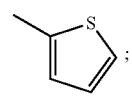

A and B are independently selected from C and N; R$_1$, R$_2$, R$_3$, and R$_4$ are independently selected from —H, halogen, —OH, and —CH$_3$; and R$_5$, R$_6$, and R$_7$ are independently selected from —H, halogen, —OH, —OCH$_3$, —NO$_2$, —N(CH$_3$)$_2$, C$_1$-C$_6$ alkyl, or a substituted or unsubstituted C$_4$-C$_6$ aryl group, except that when A and/or B is N the adjacent R$_5$ and/or R$_7$ is —H, or a pharmaceutically acceptable salt thereof.

In one aspect, the phospholipid-polymer-targeting ligand conjugate comprises the DSPE-PEG3400-XW-01-11 Conjugate or the DSPE-PEG3500-XW-01-11 Conjugate.

In one aspect, a compound is provided comprising:

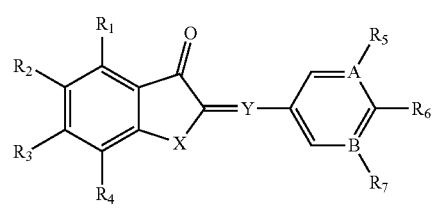

(I)

wherein X is —CH$_2$—, —CH$_2$—CH$_2$—, —CHO—, or —O—CO—; Y is —CH—CH=CH— or

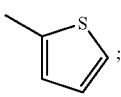

A and B are independently selected from C and N; $R_1$, $R_2$, $R_3$, and $R_4$ are independently selected from —H, halogen, —OH, and —$CH_3$; and $R_5$, $R_6$, and $R_7$ are independently selected from —H, halogen, —OH, —$OCH_3$, —$NO_2$, —$N(CH_3)_2$, $C_1$-$C_6$ alkyl, or a substituted or unsubstituted $C_4$-$C_6$ aryl group, except that when A and/or B is N the adjacent $R_5$ and/or $R_7$ is —H, or a pharmaceutically acceptable salt thereof.

In one aspect, the compound has the structure:

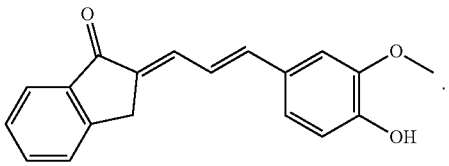 [SMILES: COc1cc(/C=C/C=C2\Cc3ccccc3C2=O)ccc1O]

In another aspect, a method for detecting α-syn aggregates is provided. The method comprises introducing into a sample or a subject an effective amount of a compound comprising:

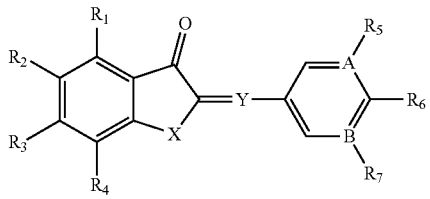

wherein X is —$CH_2$—, —$CH_2$—$CH_2$—, —CHO—, or —O—CO—; Y is —CH—CH=CH— or

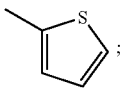

A and B are independently selected from C and N; $R_1$, $R_2$, $R_3$, and $R_4$ are independently selected from —H, halogen, —OH, and —$CH_3$; and $R_5$, $R_6$, and $R_7$ are independently selected from —H, halogen, —OH, —$OCH_3$, —$NO_2$, —$N(CH_3)_2$, $C_1$-$C_6$ alkyl, or a substituted or unsubstituted $C_4$-$C_6$ aryl group, except that when A and/or B is N the adjacent $R_5$ and/or $R_7$ is —H, or a pharmaceutically acceptable salt thereof; providing sufficient time for the compound to associate with α-syn aggregates in the sample or the subject; and detecting the compound associated with α-syn aggregates in the sample or the subject.

BRIEF DESCRIPTION OF THE FIGURES

The present invention may be more readily understood by reference to the following figures, wherein:

FIG. 12 shows a table (Table 1) of emission spectra and binding affinity ($K_d$) data for new α-syn ligands.

FIG. 14 shows a table (Table 2) of the observed bathochromic shifts in fluorescence and emission maxima, the increase in fluorescence, and fluorescence quantum yields upon fibril binding by new α-syn ligands.

FIG. 15 shows a table (Table 3) comparing dissociation constants of the new α-syn ligands to Aβ fibrils and α-syn fibrils.

DETAILED DESCRIPTION

Figure 1:
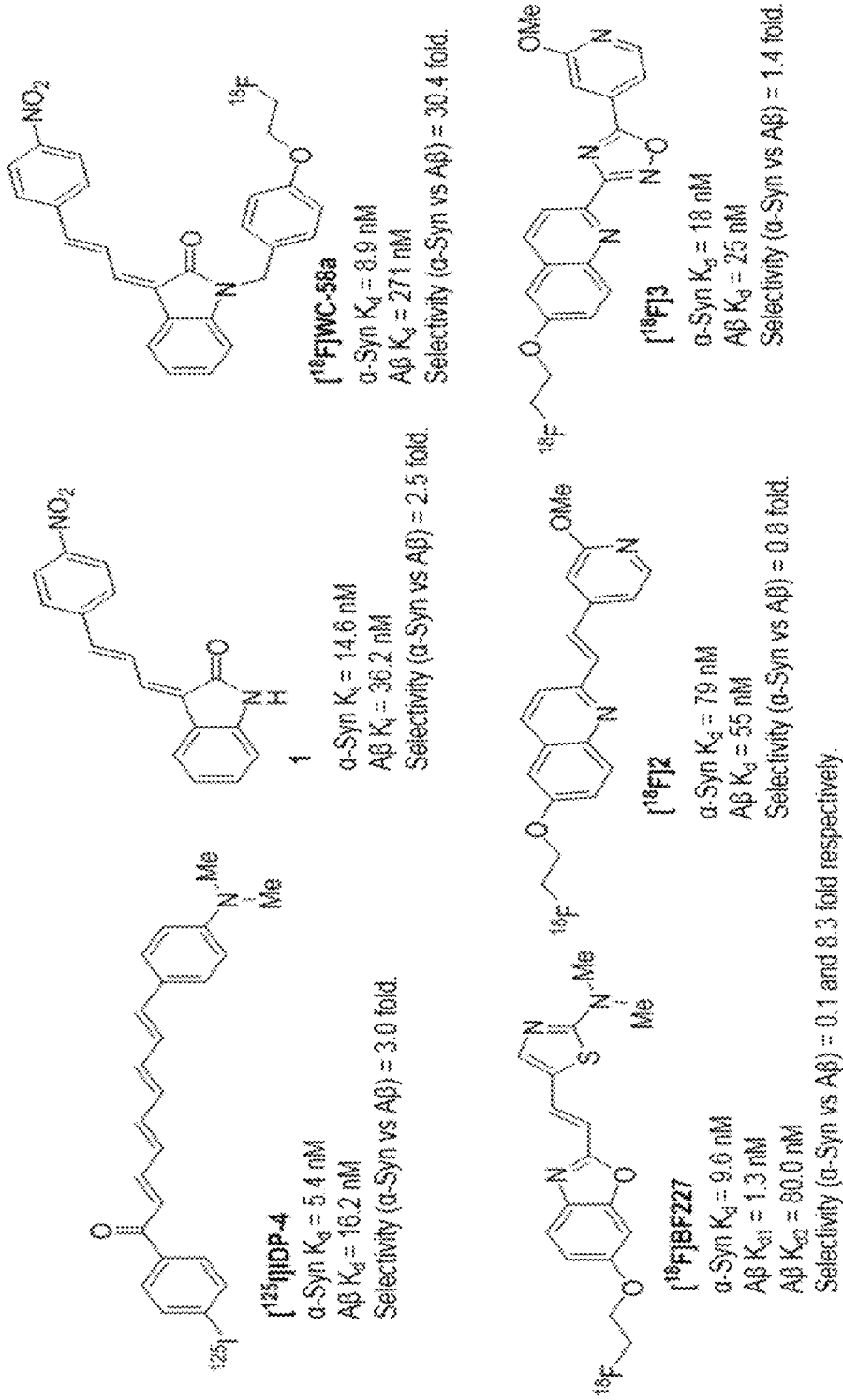
FIG. 1 provides the chemical structures of prior art representatives of α-syn aggregate binding ligands.

A novel α-syn-targeted liposomal-Gd contrast agent, ADx-003, has been developed based on a highly stable macrocyclic Gd-DOTA imaging moiety. ADx-003 may be generally understood as depicted in cross-section form in FIG. 2.

Thus, in one aspect, ADx-003 comprises a first phospholipid; a sterically bulky excipient that is capable of stabilizing the liposomal composition; a second phospholipid that is derivatized with a first polymer; a macrocyclic gadolinium-based imaging agent; and a third phospholipid that is derivatized with a second polymer, the second polymer being conjugated to a targeting ligand. The macrocyclic gadolinium-based imaging agent may be conjugated to a fourth phospholipid.

Phospholipids

In some aspects, suitable phospholipids include those where the two hydrocarbon chains are between about 14 and about 24 carbon atoms in length and have varying degrees of unsaturation. In some aspects, suitable phospholipids include HSPC, 1,2-dipalmitoyl-sn-glycero-3-phosphocholine ("DPPC"), 1,2-distearoyl-sn-glycero-3-phosphocholine ("DSPC"), 1,2-distearoyl-sn-glycero-3-phosphoethanolamine ("DSPE"), and mixtures of two or more thereof. Suitable phospholipids may be naturally occurring or synthetic.

In some aspects, suitable phospholipids may include any of those listed in WO2005107820A1, the content of paragraphs [0031]-[0033] of which is incorporated by reference herein in its entirety.

Polymer-Derivatized Phospholipids

In some aspects, the liposomes of the liposomal composition may include a surface that contains or is coated with flexible water soluble (hydrophilic) polymer chains. These polymer chains may prevent interaction between the liposomes and blood plasma components, the plasma components playing a role in uptake of liposomes by cells of the blood and removal of the liposomes from the blood. The liposomes may avoid uptake by the organs of the mononuclear phagocyte system, primarily the liver and spleen (the reticuloendothelial system).

In one aspect, the polymer in the derivatized phospholipid may be polyethylene glycol ("PEG"). The PEG can have any of a variety of molecular weights. In one example, the PEG chain may have a molecular weight between about 1,000-10,000 Daltons. Once a liposome is formed, the PEG chains may provide a surface coating of hydrophilic chains sufficient to extend the blood circulation time of the liposomes compared to the absence of such a coating.

In some aspects, the second phospholipid that is derivatized with a first polymer comprises DSPE-mPEG2000. In some aspects, the third phospholipid that is derivatized with a second polymer, the second polymer being conjugated to the targeting ligand, comprises:

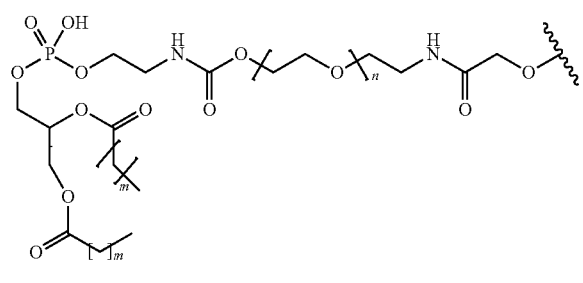

or a salt (e.g., an ammonium phosphate salt) thereof, wherein the variable n may be any integer from about 10 to about 100, for example, about 60 to about 100, about 70 to about 90, about 75 to about 85, about 77, or about 79. The variable m may be one of: 12, 13, 14, 15, 16, 17, or 18. For example, n may be 77, and m may be 14; n may be 79, and m may be 14; n may be 77, and m may be 16; and n may be 79, and m may be 16. In some aspects, the third phospholipid that is derivatized with a second polymer comprises DSPE-PEG3400 or DSPE-PEG3500.

In some aspects, suitable polymers may include any of those listed in WO2005107820A1, the content of paragraphs [0034]-[0038] of which is incorporated by reference herein in its entirety. In some aspects, the phospholipid derivatized by a polymer may be any of those combinations disclosed in WO2016057812A1 and U.S. Pat. No. 11,116,854, each of which is incorporated by reference herein in its entirety.

Sterically Bulky Excipients

In some aspects, the liposomes may include stabilizing excipients. For example, the liposomal compositions may be formulated to comprise Chol. In other aspects, the liposomal compositions may comprise fatty alcohols, fatty acids, cholesterol esters, other pharmaceutically acceptable excipients, and mixtures thereof.

Macrocyclic Gadolinium-Based Imaging Agents

The liposomal composition comprises a macrocyclic Gd-based imaging agent. In some aspects, the macrocyclic gadolinium-based imaging agent comprises Gd(III)-DOTA conjugated to a phospholipid, e.g.:

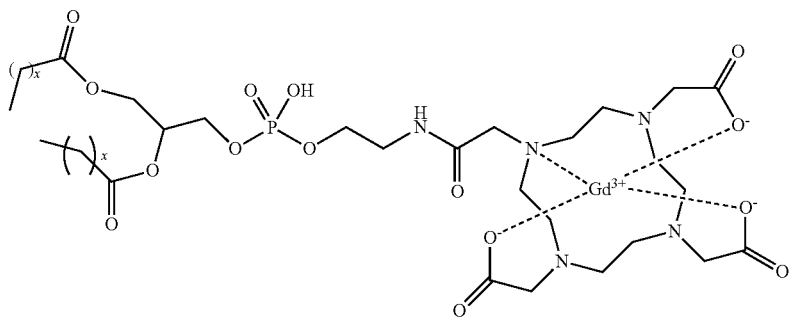

or a salt (e.g., a sodium salt) thereof. In some aspects, the variable x may be one of: 12, 13, 14, 15, 16, 17, or 18. In one aspect, the variable x is 16 and the conjugate is Gd(III)-DOTA-DSPE. Preparation of Gd(III)-DOTA-DSPE is described in U.S. Pat. No. 11,116,854.

In other aspects, the macrocyclic gadolinium-based imaging agent comprises:

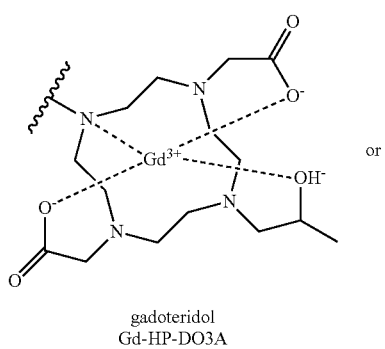

gadoteridol
Gd-HP-DO3A

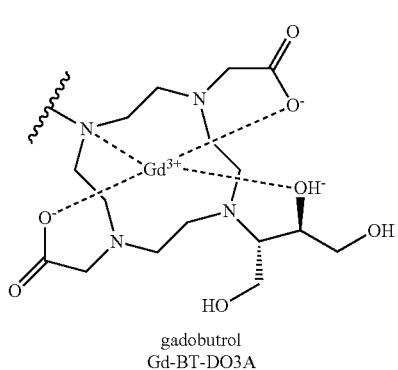

gadobutrol
Gd-BT-DO3A

Phospholipid-Polymer-Targeting Ligand Conjugate

Another aspect of the invention provides a phospholipid-polymer-targeting ligand conjugate, having a structure according to Formula II:

wherein PL is a phospholipid; AL is an aliphatic linkage; HP is a hydrophilic polymer; X is a bond, —O—, —$R_iO$—, —$R_iO(C=O)$, $R_i$—$N(R_{ii})$ O(C=O), $R_i$—$N(R_{ii})$(C=O—, or $R_i$—$N(R_{ii})$; and TL is a targeting ligand having a structure according to Formula I.

The phospholipid-polymer-targeting ligand conjugate includes a phospholipid-polymer region that facilitates incorporation of the conjugate into a membrane such as that present in a liposome. Phospholipids are amphiphilic compounds whose structures are well known to those skilled in the art. In some aspects, the phospholipid (PL) in the phospholipid-polymer-targeting ligand conjugate may be represented by the following structural formula:

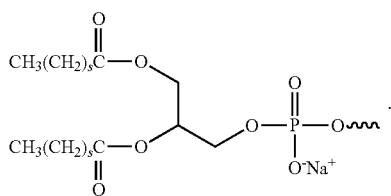

The formula illustrates the hydrophilic phosphate group and the two hydrophobic fatty acid chains commonly present in phospholipids. The variable s may be one of: 12, 13, 14, 15, 16, 17, or 18. For example, s may be 14 or 16. In various aspects, the phospholipid group in the phospholipid-polymer-targeting ligand conjugate may be one of: HSPC, DPPC, DSPE, DSPC, or DPPE. Suitable phospholipids and polymer derivatized phospholipids may also include those otherwise disclosed herein.

The conjugate also includes a hydrophilic polymer (HP). Hydrophilic polymers are polymers that contain polar or charged functional groups that render them soluble in water. Examples of hydrophilic polymers include polyacrylamides, polyethyleneimines, polyacrylic acids, polyvinyl alcohols, and polyalkylene oxides. In some aspects, the hydrophilic polymer is a poly(alkylene oxide) polymer. The hydrophilic poly(alkylene oxide) may include between about 10 and about 100 repeat units, and may have, e.g., a molecular weight ranging from 500-10,000 Daltons. The hydrophilic poly(alkylene oxide) may include, for example, PEG, poly (ethylene oxide), poly(propylene oxide), and the like. The hydrophilic polymer HP may be conjugated to the phospholipid moiety via an amide or carbamate group, as described herein. The HP in the phospholipid-polymer-targeting ligand conjugate may be conjugated to the aromatic moiety via an amide, carbamate, poly (alkylene oxide), triazole, combinations thereof, and the like.

In some aspects, the hydrophilic polymer (HP) is represented by one of the following structural formulas:

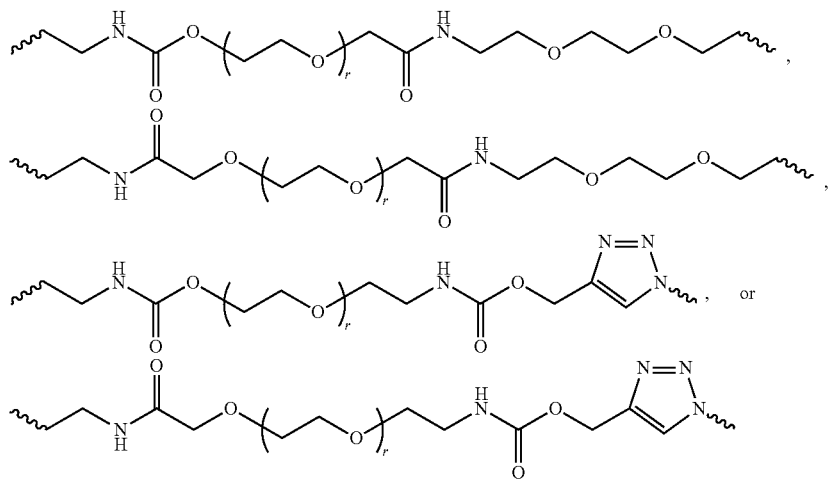

In some aspects, the variable r may be any integer from about 10 to about 100, for example, about 60 to about 100, about 70 to about 90, about 75 to about 85, about 77, or about 79.

In several aspects, the phospholipid-polymer moiety PL-HP—in the phospholipid-polymer-targeting ligand conjugate may be represented by one of the following structural formulas:

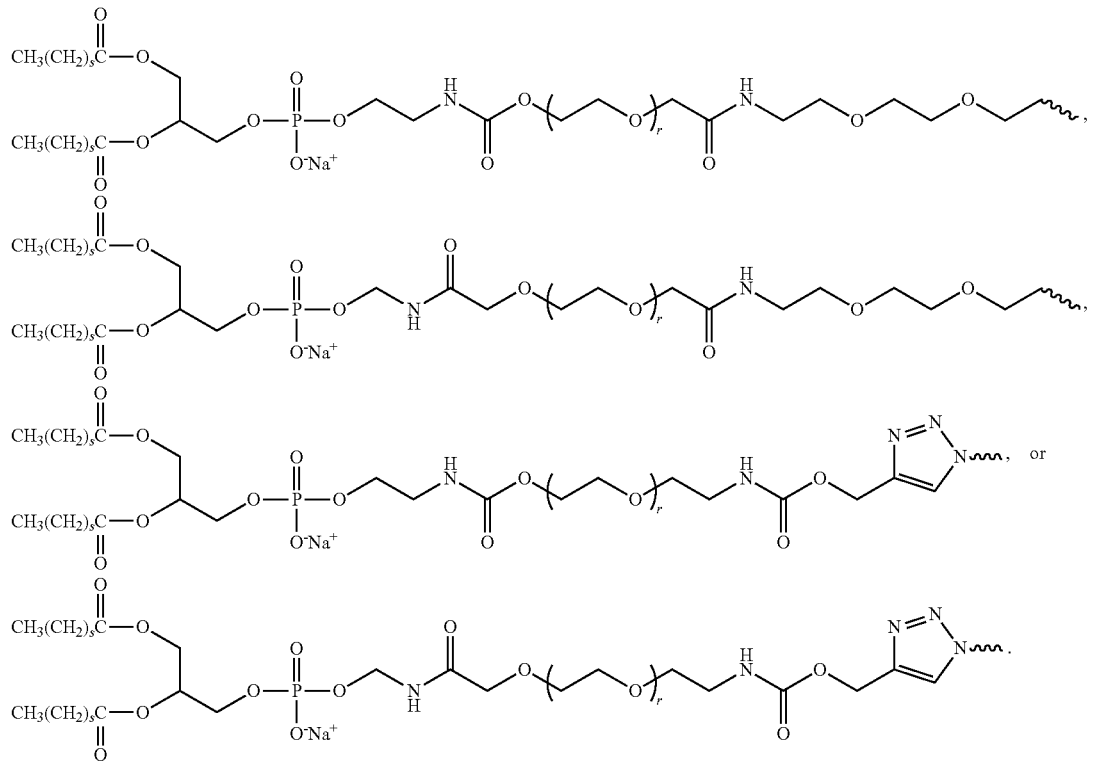

In some aspects, the variable r may be any integer from about 10 to about 100, for example, about 60 to about 100, about 70 to about 90, about 75 to about 85, about 77, or about 79. The variable s may be one of: 12, 13, 14, 15, 16, 17, or 18. For example, r may be 77, and s may be 14; r may be 79, and s may be 14; r may be 77, and s may be 16; and r may be 79, and s may be 16.

As used herein, an "aliphatic linkage" represented by AL includes any aliphatic group useful for linking between a phospholipid PL and a hydrophilic polymer HP. Such aliphatic linkages may include, for example, $C_2$-$C_{10}$ alkylene groups, which may include heteroatoms via one or more moieties such as amides, carbamates, and the like. For example, in the conjugate below:

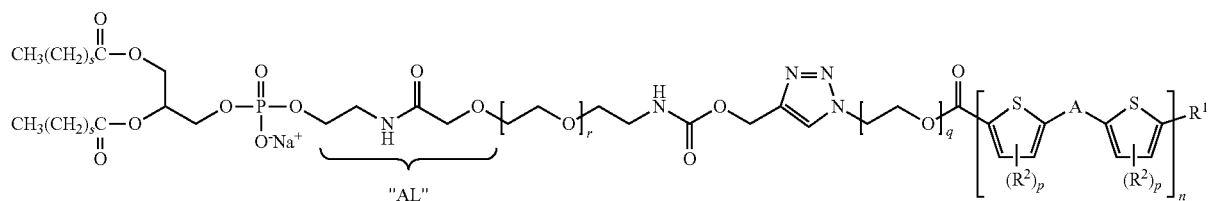

the aliphatic linkage AL, —CH$_2$CH$_2$NH(C=O)CH$_2$O—, includes an amide moiety. Further, for example, in the conjugate below:

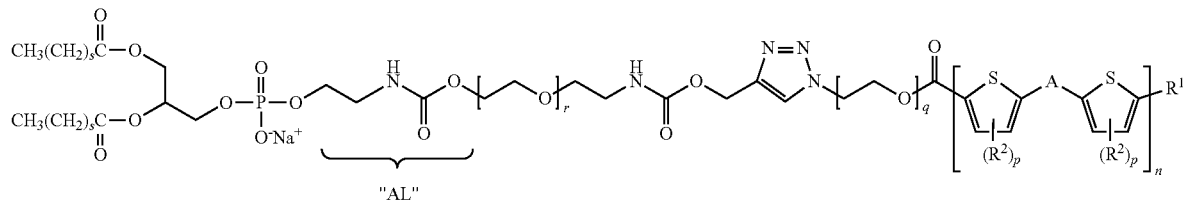

the aliphatic linkage AL, —CH$_2$CH$_2$NH(C=O)O—, includes a carbamate moiety. AL may include aliphatic linkages derived from dicarboxylic acids, such as succinic acid, and may include two amides, two carbamates, an amide and a carbamate, and the like.

Such aliphatic linkages are known in the art for linking between a phospholipid and a hydrophilic polymer, and may be found, for example, in commercial sources of phospholipid-PEG compounds, and functionalized phospholipid-PEG conjugation precursors, which may be represented as PL-AL-PEG-NH$_2$, PL-AL-PEG-CO$_2$H, and the like. It is common in the art and in commercial sources to refer to such compounds in abbreviated form without reference to the aliphatic linkage, where the presence of the aliphatic linkage is implied. For example, 1,2-distearoyl-sn-glycero-3-phosphoethanolamine-N-[methoxy(polyethylene glycol)-2000] CAS No. 147867-65-0, in which the aliphatic linking group is the amide containing group —CH$_2$CH$_2$NH(C=O)CH$_2$O—, is commonly referred to in the art and commercially as "DSPE-mPEG-2000." Commercial materials recited herein in the conventional abbreviated manner, such as "DSPE-mPEG-2000," should be understood to include corresponding aliphatic linkages.

Accordingly, in various aspects, the aliphatic linker represented by AL may include a carbamate or an amide. The liposomes, methods, and conjugates described herein may include phospholipid-polymer-targeting ligand conjugates wherein AL includes a carbamate, an amide, or a mixture of such conjugates.

In one specific aspect, a phospholipid-polymer-targeting ligand conjugate is provided, the phospholipid-polymer aspect of the phospholipid-polymer-targeting ligand conjugate comprising:

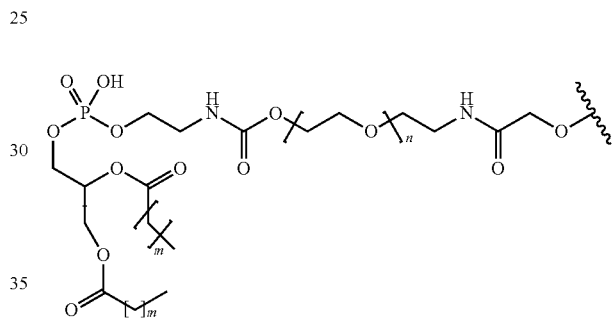

or a salt (e.g., an ammonium phosphate salt) thereof. In some aspects, the variable n may be any integer from about 10 to about 100, for example, about 60 to about 100, about 70 to about 90, about 75 to about 85, about 77, or about 79. The variable m may be one of: 12, 13, 14, 15, 16, 17, or 18. For example, n may be 77, and m may be 14; n may be 79, and m may be 14; n may be 77, and m may be 16; and n may be 79, and m may be 16. In some aspects, the phospholipid-polymer aspect of the phospholipid-polymer-targeting ligand conjugate comprises DSPE-PEG3400 or DSPE-PEG3500.

The phospholipid-polymer-targeting ligand conjugate of Formula II also includes a targeting ligand (TL), which is discussed below.

Targeting Ligands

The liposome compositions comprise at least one phospholipid that is derivatized with a polymer, the polymer being conjugated to a targeting ligand. Thus, in some aspects, the phospholipid is modified to include a spacer chain. The spacer chain may be a hydrophilic polymer. The hydrophilic polymer may typically be end-functionalized for coupling to the targeting ligand. The functionalized end group may be, for example, a maleimide group, a bromoacetamide group, a disulfide group, an activated ester, or an aldehyde group. Hydrazide groups are reactive toward aldehydes, which may be generated on numerous biologically relevant compounds. Hydrazides may also be acylated by active esters or carbodiimide-activated carboxyl groups. Acyl azide groups reactive as acylating species may be easily obtained from hydrazides and permit the attachment of amino containing ligands.

In some aspects, the targeting ligand may be accessible from the surface of the liposome and may specifically bind or attach to, for example, one or more molecules or antigens. These targeting ligands may direct or target the liposomes to a specific cell or tissue, e.g., an α-syn plaque, and may bind to a molecule or antigen on or associated with the cell or tissue.

In one aspect, a compound is provided according to Formula I:

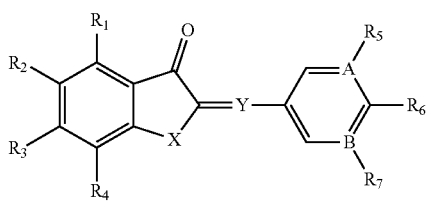

wherein X is —CH$_2$—, —CH$_2$—CH$_2$—, —CHO—, or —O—CO—; Y is —CH—CH=CH— or

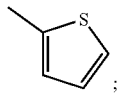
;

A and B are independently selected from C and N; $R_1$, $R_2$, $R_3$, and $R_4$ are independently selected from —H, halogen, —OH, and —CH$_3$; and $R_5$, $R_6$, and $R_7$ are independently selected from —H, halogen, —OH, —OCH$_3$, —NO$_2$, —N(CH$_3$)$_2$, $C_1$-$C_6$ alkyl, or a substituted or unsubstituted $C_4$-$C_6$ aryl group, except that when A and/or B is N the adjacent $R_5$ and/or $R_7$ is —H, or a pharmaceutically acceptable salt thereof. The compounds of Formula I are sometimes interchangeably referred to herein as "targeting ligands" and "binding ligands." The targeting ligands exhibit high affinity binding to α-syn, and in particular, misfolded α-syn, such as that found in deposits (also referred to herein as plaques) or fibrils.

Compounds included in Formula I may vary at position X to provide different heterocyclic compounds. In some aspects, X is —CH$_2$—, which provides a 1-indanone heterocyclic group. In some aspects, X is —CH$_2$—CH$_2$—, which provides a tetralone heterocyclic group. In some aspects, X is —CHO—, which provides a 1,3-indandione heterocyclic group. In further aspects, X is —O—CO—, which provides a 4-hydroxycoumarin heterocyclic group. This heterocyclic group is sometimes referred to herein as the "first aromatic group."

Compounds included in Formula I may vary at position Y to provide different dienes. Thus, in one aspect, Y is —CH—CH=CH—, and a diene bridge is provided. In one aspect, the diene bridge has an E,E configuration. In other aspects, Y is

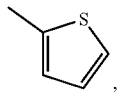
, thereby implementing the diene in the form of an electron-rich thiophene group.

In some aspects, the second (right-most) aromatic group of the compound may be modified. Modification within the ring may include replacement of a methylidyne at position A or B with a nitrogen atom to provide a pyridine as the second aromatic group; or it may include replacement of a methylidyne at position A and B with a nitrogen atom to provide a pyrimidine as the second aromatic group. When position A, B, or both have been replaced with a nitrogen, the position undergoing the replacement will not have a substituent external to the ring.

Compounds included in Formula I may also include compounds in which one or more substituents have been added around the first and/or second aromatic rings. Examples of suitable substituents include halogen, hydroxyl, methoxy, nitro, dimethylamine, and lower alkyl or aryl moieties. For example, in some aspects, a hydrogen atom along the circumference of the second aromatic ring is replaced with a para-substituted phenyl group.

Figure 3:
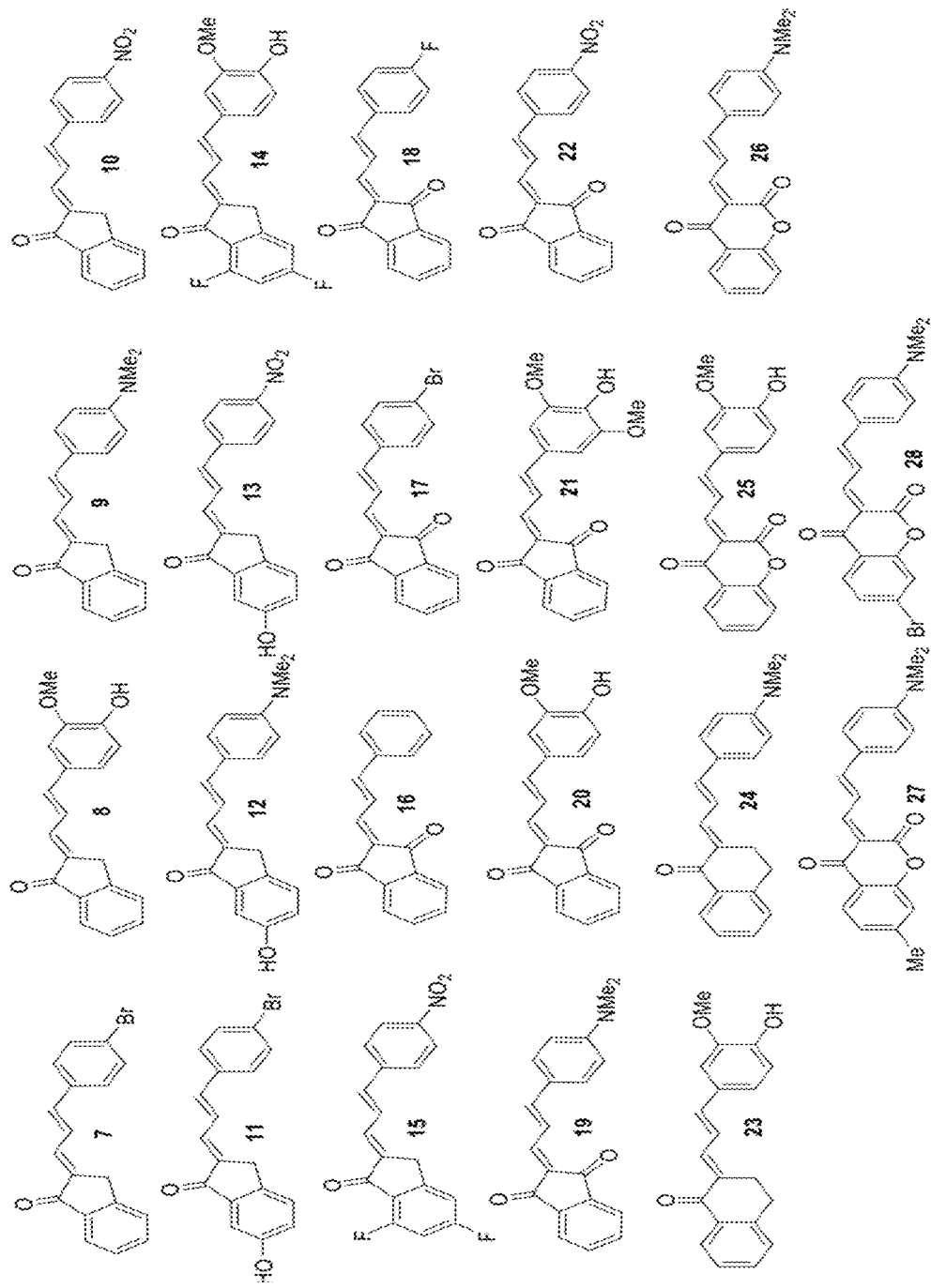
FIG. 3 provides the chemical structures of new α-syn ligands, including 1-indanonyl-, 1,3-indandionyl-, α-tetralonyl-, and 4-oxocoumarinyl-diene derivatives.
Figure 8:
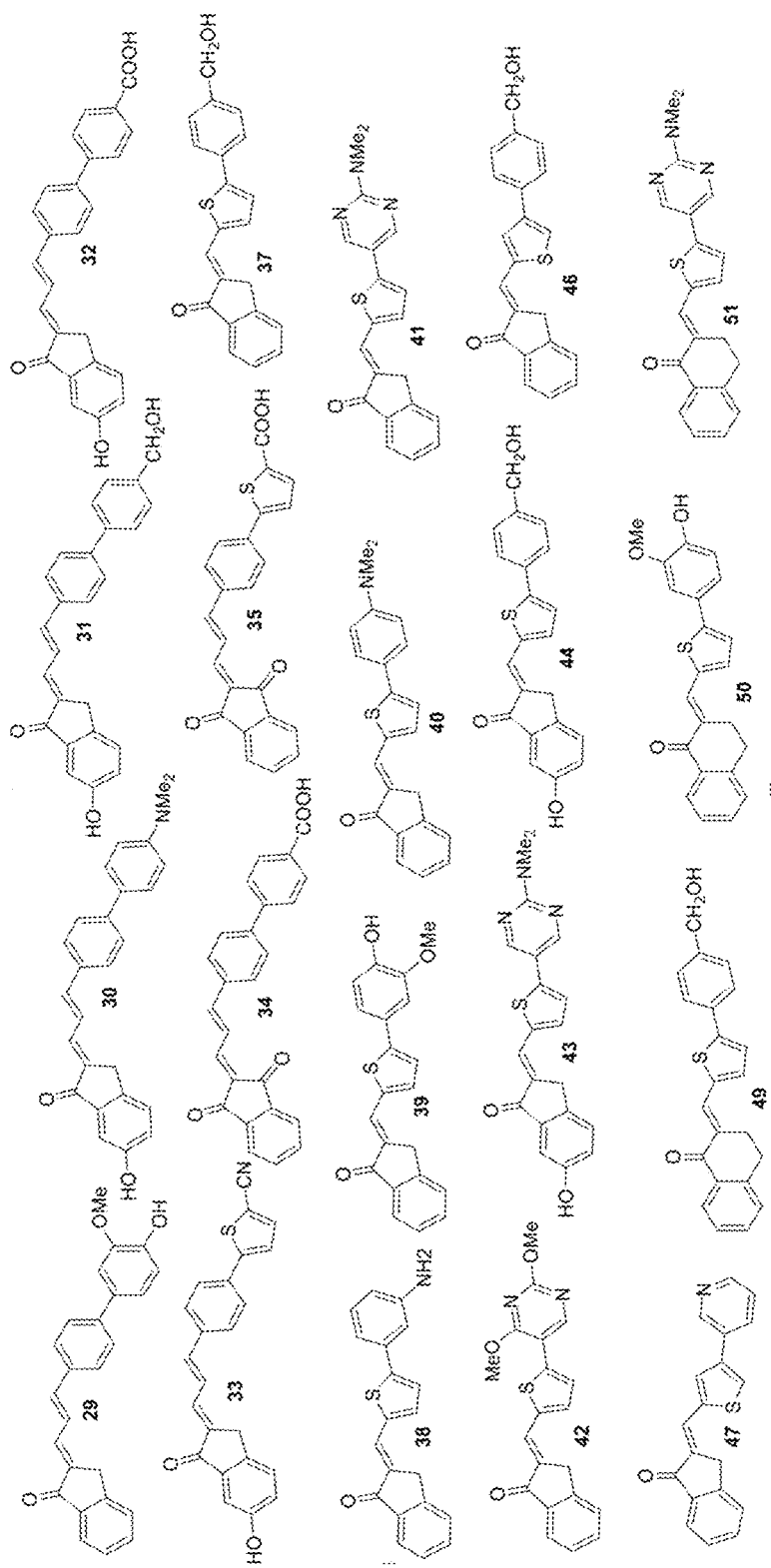
FIG. 8 provides the chemical structures of new α-syn ligands, including 1-indanonyl- and 1,3-indandionyl-diene derivatives with thiophene inserted into the diene bridge.

Suitable compounds included in Formula I may include, for example, with reference to FIG. 3 and FIG. 8, compounds 8 ((E)-2-((E)-3-(4-Hydroxy-3-methoxyphenyl)allylidene)-2,3-dihydro-1H-inden-1-one), 32 (4'-((E)-3-((E)-6-Hydroxy-1-oxo-1,3-dihydro-2H-inden-2-ylidene)prop-1-en-1-yl)-[1,1'-biphenyl]-4-carboxylic acid), and 37 ((Z)-2-((5-(4-(Hydroxymethyl)phenyl)thiophen-2-yl)methylene)-2,3-dihydro-1H-inden-1-one).

In some aspects, the compound is compound 8:

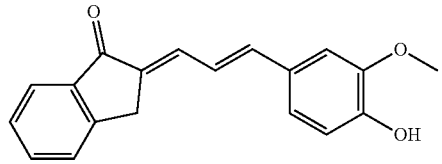 [SMILES: COc1cc(/C=C/C=C2\Cc3ccccc3C2=O)ccc1O]

The binding ligands of Formula I include compounds that have a high affinity for α-syn, such as the α-syn present in deposits and fibrils. In particular, since the α-syn present in fibrils and deposits is typically aggregated α-syn, the binding ligands have a high affinity for aggregated α-syn. In some aspects, the compounds are α-syn specific. In some aspects, the compounds have a higher affinity for α-syn than for Aβ. α-Syn-specific, as used herein, refers to the fact that imaging agents bind to α-syn exclusively or preferentially compared to other proteins that are associated with misfolded protein diseases and disorders. As used herein, the term "specifically binding" refers to the interaction of the binding ligand with a second chemical species, wherein the interaction is dependent upon the presence of a particular structure (e.g., an antigenic determinant or epitope) on the chemical species. For example, the targeting ligand recognizes and binds to a specific protein structure of α-syn rather than to proteins generally.

Compounds within the scope of Formula I have various different binding affinities for α-syn (e.g., aggregated α-syn). In some aspects, the compounds have a binding affinity for aggregated α-syn with a $K_d$ of about 500 nM or less. In some aspects, the compounds have a binding affinity for aggregated α-syn with a $K_d$ of about 200 nM or less. In other aspects, the compounds have a binding affinity for aggregated α-syn with a $K_d$ of about 100 nM or less. In further aspects, the compounds have a binding affinity for aggregated α-syn with a $K_d$ of about 50 nM or less.

In some aspects, the compounds further comprise a radiolabel. A radiolabeled compound has one or more atoms replaced with a radionuclide. Examples of radiolabels include $^{3}H$, $^{14}C$, $^{35}S$, $^{125}I$, $^{121}I$, $^{112}In$, $^{99m}Tc$. Compounds can also be modified to include atoms useful in positron emission tomography, such as $^{18}F$, $^{11}C$, and $^{15}O$.

Suitable compounds included in Formula I may exist as pharmaceutically acceptable salts, e.g., acid addition salts, including those formed with organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable.

The term "pharmaceutically acceptable salt," as used herein, represents salts or zwitterionic forms of the compounds included in Formula I that are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Basic groups in the compounds may be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids that can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, sodium, potassium, magnesium, and calcium salts of the compounds of Formula I are contemplated.

Liposomes

Figure 2:
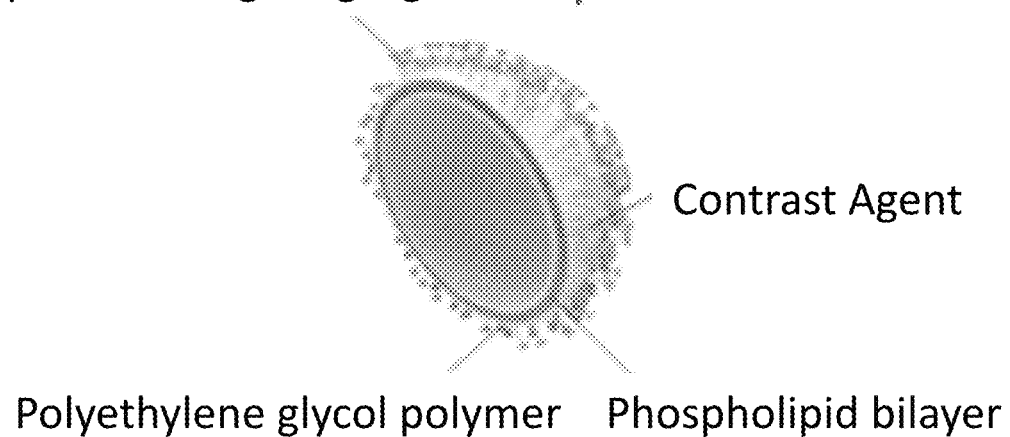
FIG. 2 provides an example cross-sectional depiction of a liposome comprising a targeted contrast agent for MRI of α-syn deposition.

"Liposomes" generally refer to spherical or roughly spherical particles containing an internal cavity. The walls of liposomes may include a bilayer of lipids. These lipids can be phospholipids. Numerous lipids and/or phospholipids may be used to make liposomes. One example are amphipathic lipids having hydrophobic and polar head group moieties, which may form spontaneously into bilayer vesicles in water, as exemplified by phospholipids, or which may be stably incorporated into lipid bilayers, with their hydrophobic moiety in contact with the interior, hydrophobic region of the bilayer membrane, and their polar head group moiety oriented toward the exterior, polar surface of the membrane. Liposomes may be prepared by any known method, including as described in the Examples herein, and in U.S. Pat. No. 11,116,854, WO2016057812A1, and WO2012139080A1, each which is incorporated by reference herein in its entirety. FIG. 2 provides an example cross-sectional depiction of a liposome comprising a targeted contrast agent for MRI of α-syn deposition.

In one aspect, ADx-003 comprises: HSPC; Chol; DSPE-mPEG2000; DSPE-PEG3400-XW-01-11 Conjugate; and Gd(III)-DOTA-DSPE. In one aspect, ADx-003 comprises: HSPC; Chol; DSPE-mPEG2000; DSPE-PEG3500-XW-01-11 Conjugate; and Gd(III)-DOTA-DSPE. In some aspects, the first phospholipid may comprise DPPC, DSPC, or a mixture of DPPC and DSPC. In one aspect, the lipid composition and molar ratio (%) of components in ADx-003 are HSPC:Chol:DSPE-mPEG2000:Gd(III)-DOTA-DSPE: DSPE-PEG3400/3500-Formula I conjugate=about 31.5: about 40: about 2.5: about 25: about 1. In some aspects, the molar ratio of any one of HSPC:Chol:DSPE-mPEG2000: Gd(III)-DOTA-DSPE:DSPE-PEG3400/3500-Formula I conjugate may be adjusted by up to 10%, thus, 31.5±10%: 40±10%: 2.5±10%: 25±10%:1±10%. In one aspect, the lipid composition and molar ratio (%) of components in ADx-003 are HSPC:Chol:DSPE-mPEG2000:Gd(III)-DOTA-DSPE: DSPE-PEG3400/3500-Formula I conjugate=about 32.5: about 40: about 2: about 25: about 0.5. In one aspect, the lipid composition and molar ratio (%) of components in ADx-003 are HSPC:Chol:DSPE-mPEG2000:Gd(III)-DOTA-DSPE:DSPE-PEG3400/3500-Formula I conjugate=about 32: about 40: about 2.5: about 25: about 0.5.

In one aspect, the HSPC content in ADx-003 is between about 24 mg/mL and about 32 mg/mL (total lipid). In one aspect, the Chol content in ADx-003 is between about 14 mg/mL and about 19 mg/mL. In one aspect, the DSPE-mPEG2000 content in ADx-003 is between about 5 mg/mL and about 7 mg/mL. In one aspect, the Gd(III)-DOTA-DSPE content in ADx-003 is between 30 mg/mL and 45 mg/mL. In one aspect, the DSPE-PEG3400/3500-Formula I conjugate content in ADx-003 is between about 2 mg/mL and about 3 mg/mL. In one aspect, the free gadolinium content in ADx-003 is ≤100 µg/mL, including <2.5 µg/mL.

In one aspect, the liposomal composition has a pH of between 6.4 and 8.4. In a further aspect, the liposomes have an osmolality of between 200-400 mOsmol/kg. In a further aspect, the liposomes have vesicle size (Z-average) as measured by dynamic light scattering of less than about 200 nm ($D_{50}$), including less than 150 nm ($D_{50}$), including about 140 nm ($D_{50}$), and including about 120 nm ($D_{50}$).

To be clear, the term "about" in conjunction with a number is intended to include ±10% of the number. This is true whether "about" is modifying a stand-alone number or modifying a number at either or both ends of a range of numbers. In other words, "about 10" means from 9 to 11. Likewise, "about 10 to about 20" contemplates 9 to 22 and 11 to 18. In the absence of the term "about," the exact number is intended. In other words, "10" means 10.

Methods for Detecting α-Syn

A method is provided for detecting α-syn (e.g., aggregated α-syn). The method comprises introducing into a sample or a subject an effective amount of a compound according to Formula I:

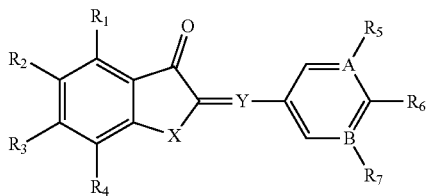

wherein X is —CH₂—, —CH₂—CH₂—, —CHO—, or —O—CO—; Y is —CH—CH=CH— or

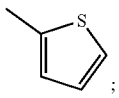

A and B are independently selected from C and N; R₁, R₂, R₃, and R₄ are independently selected from —H, halogen, —OH, and —CH₃; and R₅, R₆, and R₇ are independently selected from —H, halogen, —OH, —OCH₃, —NO₂, —N(CH₃)₂, C₁-C₆ alkyl, or a substituted or unsubstituted C₄-C₆ aryl group, except that when A and/or B is N the adjacent R₅ and/or R₇ is —H, or a pharmaceutically acceptable salt thereof. The method also comprises the steps of providing sufficient time for the compound to associate with α-syn in the sample or the subject, and detecting the compound associated with α-syn in the sample or the subject.

In some aspects, α-syn may refer to full-length, 140 amino acid α-synuclein protein, e.g., "α-syn-140." Other isoforms or fragments may include, for example, "α-syn-126," alpha-synuclein-126, which lacks residues 41-54, e.g., due to loss of exon 3; and "α-syn-112" alpha-synuclein-112, which lacks residue 103-130, e.g., due to loss of exon 5.

α-Syn aggregates form insoluble fibrils in pathological conditions characterized by LB, such as PD, DLB, MSA, and PAF. α-Syn is the primary structural component of LB fibrils. α-Syn may be present in brains of individuals suffering from PD or suspected of having PD. Various α-syn peptides may be associated with neuronal damage associated with PD. Various α-syn isoforms associated with disease include and are not limited to α-syn-140, α-syn-126, and α-syn-112.

The compound used in the method of detection can be any of the α-syn targeting ligands according to Formula I. For example, in some aspects, the targeting ligand is a compound of Formula I in which Y is —CH—CH=CH—, while in further aspects the targeting ligand is a compound of Formula I wherein A and B are both carbon atoms. In further aspects, the targeting ligand is selected from compound 8, compound 32, and compound 37 of FIG. 3 and FIG. 8, while in yet further aspects the compound has the structure:

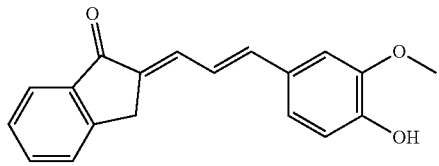 [SMILES: COc1cc(/C=C/C=C2\Cc3ccccc3C2=O)ccc1O]

In some aspects, the compound used in the method of detection is linked to a phospholipid-polymer to form a phospholipid-polymer-targeting ligand conjugate of Formula II. The phospholipid-polymer-targeting ligand conjugates can include any of the phospholipids (PL) and hydrophilic polymers (HP) described herein. The phospholipid-polymer-targeting ligand conjugates can be incorporated in a liposome. While the compounds of Formula I may be detected directly through fluorescence, may be modified to include a radiolabeled compound, or may be detected through other means, incorporating the compound into a liposome may increase the options for detection.

The method includes the step of introducing into a sample or a subject an effective amount of a compound according to Formula I. A sample may be a portion of tissue that may include α-syn, such as a tissue sample (e.g., a neural tissue sample) obtained from a subject, in which case the method is used for ex vivo analysis. Introducing the compound into the sample simply refers to contacting the sample with the compound. Alternately, the compound may be introduced into a subject in order to carry out an in vivo analysis. A "subject," as used herein, can be any animal, and may also be referred to as the patient. The subject may be a vertebrate animal, a mammal, such as a research animal (e.g., a mouse or rat), a domesticated farm animal (e.g., cow, horse, pig), or a pet (e.g., dog, cat). In some aspects, the subject is a human.

The method may also include the steps of providing sufficient time for the compound to associate with α-syn (e.g., aggregated α-syn) in the sample or the subject. The binding ligands of Formula I have an affinity for α-syn, and in particular, aggregated α-syn, and will therefore associate with α-syn present in a sample or a subject. The amount of time necessary for the compound to associate with the α-syn can vary depending on a number of variables, such as the nature of the sample, the method of administration, and the affinity of the compound being used. The amount of time sufficient for the compound to associate with α-syn can be readily determined by one skilled in the art. For example, the amount of time sufficient for the compound to associate with α-syn in a sample or in a subject can be at least 2 minutes, 5 minutes, 10 minutes, 15 minutes, 30 minutes, one hour, two hours, three hours, four hours, six hours, or at least 8 hours.

The method may include the step of detecting the compound associated with α-syn (e.g., aggregated α-syn) in the sample or the subject. In some aspects, the detecting may include detecting using MRI. In another example, the detecting may include detecting by fluorescence imaging ("FI"). The detecting may include detecting by SPECT imaging and/or PET imaging using a radioactive contrast enhancing agent. The radioactive contrast enhancing agent may include, for example, those agents deemed appropriate for use with SPECT imaging and/or PET imaging in the National Institute of Health's Molecular Imaging and Contrast Agent Database. Any other suitable type of imaging methodology known by those skilled in the art is contemplated, including, but not limited to, PET imaging.

In some aspects, an image is generated showing the location of the detected α-syn (e.g., aggregated α-syn) in the subject. Accordingly, in some aspects, a method is provided for generating an image of a tissue region of a subject, by administering to the subject an effective amount of an imaging agent (i.e., a targeting ligand or phospholipid-polymer-targeting ligand conjugate) and generating an image of the tissue region of the subject to which the imaging agent has been distributed. To generate an image of the tissue region, it is necessary for a detectably effective amount of imaging agent to reach the tissue region of interest, but it is not necessary that the imaging agent be localized in this region alone. However, in some aspects, the imaging agents are targeted or administered locally such that they are present primarily in the tissue region of interest. Examples of images include two-dimensional cross-sectional views and three-dimensional images. In some aspects, a computer is used to analyze the data generated by the imaging agents in order to generate a visual image. One example method for generating an image is MRI. MRI scanners use strong magnetic fields, magnetic field gradients, and radio waves to generate images of the organs in the body.

Imaging systems typically includes three basic components: (1) an appropriate source for inducing excitation of the imaging agent; (2) a system for separating or distinguishing emissions from the imaging agent; and (3) a detection system. The detection system can be hand-held or incorporated into other useful imaging devices, such as intraoperative microscopes. Example detection systems include an endoscope, catheter, tomographic system, hand-held imaging system, or an intraoperative microscope.

Many of the targeting ligands exhibit a higher affinity for α-syn (e.g., aggregated α-syn) than for other proteins that are involved in protein misfolding disorders, such as Aβ or tau protein. Because of this higher affinity, the binding ligands, either alone or when present in a phospholipid-polymer-targeting ligand conjugate, are capable of distinguishing levels of α-syn from the levels of other proteins that are subject to misfolding. In particular, there is an interest in distinguishing levels of aggregated α-syn from levels of aggregated Aβ. Accordingly, in some aspects, α-syn is detected with a specificity that is greater than the detection of Aβ. In other aspects, α-syn is detected with a specificity that is 1.5× or more greater than the detection of Aβ, 2× or more greater than the detection of Aβ, 3× or more greater than the detection of Aβ, 5× or more greater than the detection of Aβ, or 10× or more greater than the detection of Aβ.

In some aspects, the method for detecting and/or imaging α-syn (e.g., aggregated α-syn) in a sample or subject can be used to diagnose whether a subject has a disease associated with misfolded α-syn, or to evaluate the progression of disease in a subject. In some aspects, the subject may be at risk of developing a synucleinopathy, of having a synucleinopathy, or being under treatment for a synucleinopathy; at risk of having a disease associated with dysregulation, misfolding, aggregation, or disposition of α-syn, such as PD, LBD, MSA, or PAF; having a disease associated with dysregulation, misfolding, aggregation or disposition of α-syn; under treatment for a disease associated with dysregulation, misfolding, aggregation, or disposition of α-syn; and the like.

The method may include diagnosing a synucleinopathy in the subject based on detecting α-syn protein (e.g., aggregated α-syn). α-Syn misfolding and aggregation have been shown to be associated with PD. LBD, MSA, and PAF pathogenesis. A diagnosis of these α-syn protein misfolding disorders may also include comparing the image or the amount of α-syn protein detected to a control sample or image taken from a healthy subject. The method may include determining or diagnosing the presence of a disease associated with α-syn aggregation in the subject according to the presence of the soluble, misfolded α-syn protein in sample or subject.

In some aspects, the method includes treating a subject diagnosed as having a disease associated with α-syn aggregation with α-syn modulating therapy. Several novel therapeutics that target α-syn homeostasis through various mechanisms are currently under development. The α-syn modulating therapy may include inhibiting the production of α-syn, inhibiting the aggregation of α-syn, e.g., with a suitable inhibitor, active or passive immunotherapy approaches, and the like. Therapeutic approaches targeting α-syn homeostasis may include active immunization, such as PD01A+ or PD03A+, or passive immunization such as PRX002. The method described herein for detecting the presence of soluble, misfolded α-syn can be employed to determine which patients may be treated with an α-syn modulating therapy. While there is currently no cure for PD, a variety of drugs are useful for treating the motor symptoms of PD, such as levodopa, dopamine agonists, and monoamine oxidase B inhibitors.

The phospholipid-polymer-targeting ligand compounds including an imaging agent may be administered together with a pharmaceutically acceptable carrier. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringe-ability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

Kits for Detecting α-Syn

Another aspect of the invention provides a kit for detecting and/or imaging α-syn (e.g., aggregated α-syn) in a subject. A kit generally includes a package with one or more containers holding the targeting ligand and other components and reagents, as one or more separate compositions or, optionally, as an admixture where the compatibility of the reagents will allow. The kit may include instructions and the liposomal composition. The instructions may direct a user to introduce into the sample or the subject a detectable quantity of the liposomal composition. The instructions may direct the user to allow sufficient time for the liposomal composition to be associated with α-syn. The instructions may direct the user to detect the liposomal composition associated with the α-syn. The kit may include a targeting ligand of Formula I and/or the phospholipid-polymer-targeting conjugate represented by Formula II.

Instructions included in kits can be affixed to packaging material or can be included as a package insert. While the instructions are typically written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

Components of the kits may be in different physical states. For example, some components may be lyophilized and some in aqueous solution. Some may be frozen. Individual components may be separately packaged within the kit. Other useful tools for performing the methods of the invention or associated testing, therapy, or calibration may also be included in the kits, including buffers, enzymes, fluorescent reagents, enhancing agents (e.g., paramagnetic ions) for MRI, gels, plates, detectable labels, vessels, etc. Kits may also include a sampling device for obtaining a biological sample from a subject, such as a syringe or needle.

The term "effective amount" is intended to qualify the number or amount of the compound (e.g., the α-syn targeting ligand) which will be effective for carrying out the associated method. For example, an effective amount of the α-syn targeting ligand, or a conjugate including the α-syn targeting ligand, that will associate with α-syn present in the sample or the subject at a detectable level. When used in a subject, an effective amount may be low enough to minimize undesirable side effects associated with administration. A therapeutically effective amount may be administered in one or more doses.

The invention is inclusive of the compounds described herein in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. The term "compound" includes any or all of such forms, whether explicitly stated or not (although at times, "salts" are explicitly stated).

The term "diagnosis" can encompass determining the likelihood that a subject will develop a disease or the existence or nature of disease in a subject. The term diagnosis also encompasses determining the severity and probable outcome of disease or episode of disease or prospect of recovery, which is generally referred to as prognosis. "Diagnosis" can also encompass diagnosis in the context of rational therapy, in which the diagnosis guides therapy, including initial selection of therapy, modification of therapy (e.g., adjustment of dose or dosage regimen), and the like.

Where a range of values is provided, each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

All scientific and technical terms used in the present application have meanings commonly used in the art unless otherwise specified. The definitions provided herein are to facilitate understanding of certain terms used frequently herein and are not meant to limit the scope of the present application.

The present invention is illustrated by the following examples. The particular examples, materials, amounts, and procedures are to be interpreted broadly in accordance with the scope and spirit of the invention as set forth herein.

EXAMPLES

All reagents were obtained from Sigma-Aldrich, TCI, Alfa Aesar, or Acros Organics, and used without further purification. Proton nuclear magnetic resonances ($^1$H NMR) were recorded at 600 MHz or 500 MHz on Bruker 600 or 500 NMR spectrometers. Carbon nuclear magnetic resonances ($^{13}$C NMR) were recorded at 75 MHz or 125 MHz on a Bruker 300 or 500 NMR spectrometers respectively. Chemical shifts are reported in parts per million (ppm) from an internal standard of acetone (2.05 ppm), chloroform (7.26 ppm), or dimethylsulfoxide (2.50 ppm) for $^1$H NMR; and from an internal standard of either residual acetone (206.26 ppm), chloroform (77.00 ppm), or dimethylsulfoxide (39.52 ppm) for $^{13}$C NMR. NMR peak multiplicities are denoted as follows: s (singlet), d (doublet), t (triplet), q (quartet), dd (doublet of doublet), td (doublet of triplet), dt (triplet of doublet), and m (multiplet). Coupling constants (J) are given in hertz (Hz). High resolution mass spectra were obtained from The Ohio State University Mass Spectrometry and Proteomics Facility. TLC was performed on silica gel 60 F254 plates from EMD Chemical Inc., and components were visualized by ultraviolet light (254 nm) and/or phosphomolybdic acid, 20 wt % solution in ethanol. SiliFlash silica gel (230-400 mesh) was used for all column chromatography.

Example 1: Molecular Design of Targeting Ligands

Figure 4:
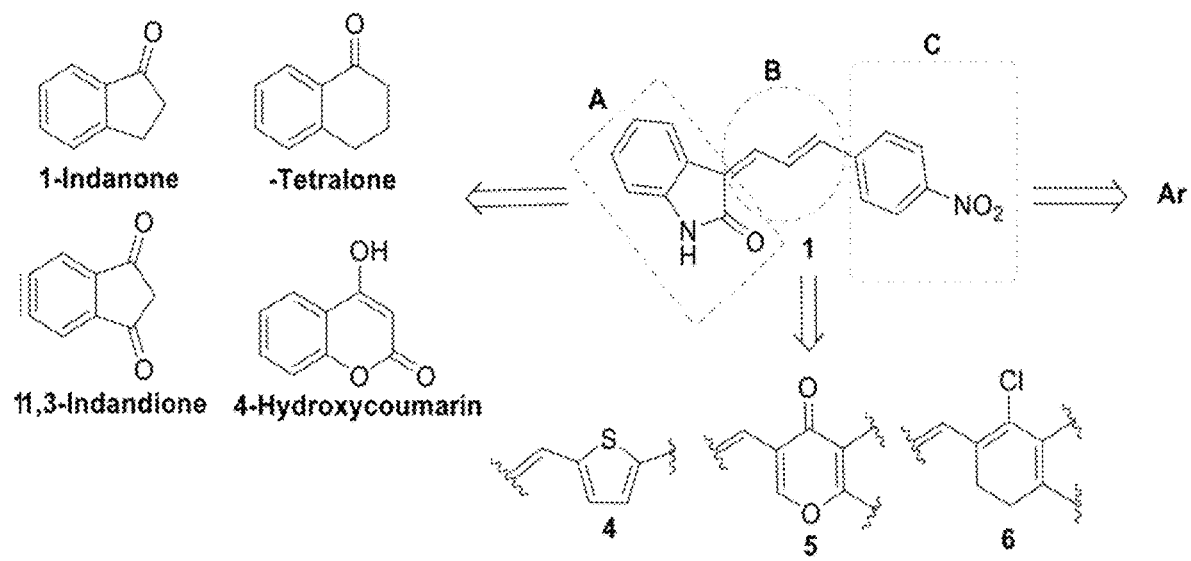
FIG. 4 provides a schematic representation of the molecular design of new α-syn ligands.

Prior art compound 1 (see FIGS. 1, 4) was chosen as a scaffold for structure activity relationship ("SAR") studies toward the development of new structures with high affinity and selectivity for α-syn aggregates. Molecular design (FIG. 4) was directed at three parts of the molecule: the first aromatic group (A), the bridge (B), and the second aromatic group (C). For (A), 1-indanone and 1,3-indandione were selected as the starting points for new derivatives. For (B), a diene was maintained in some derivatives. Derivatives were also introduced wherein one of the double bonds was replaced with an electron-rich thiophene moiety to increase the electron density within the molecule. In addition, derivatives with overall increased rigidity within the molecule were introduced by "locking" the second double bond in two different ring systems. Derivatization around second aromatic group (C) included both electron-rich and electron-deficient aromatic rings as well as heterocycles.

Example 2: Chemical Synthesis of Targeting Ligands

Figure 5:
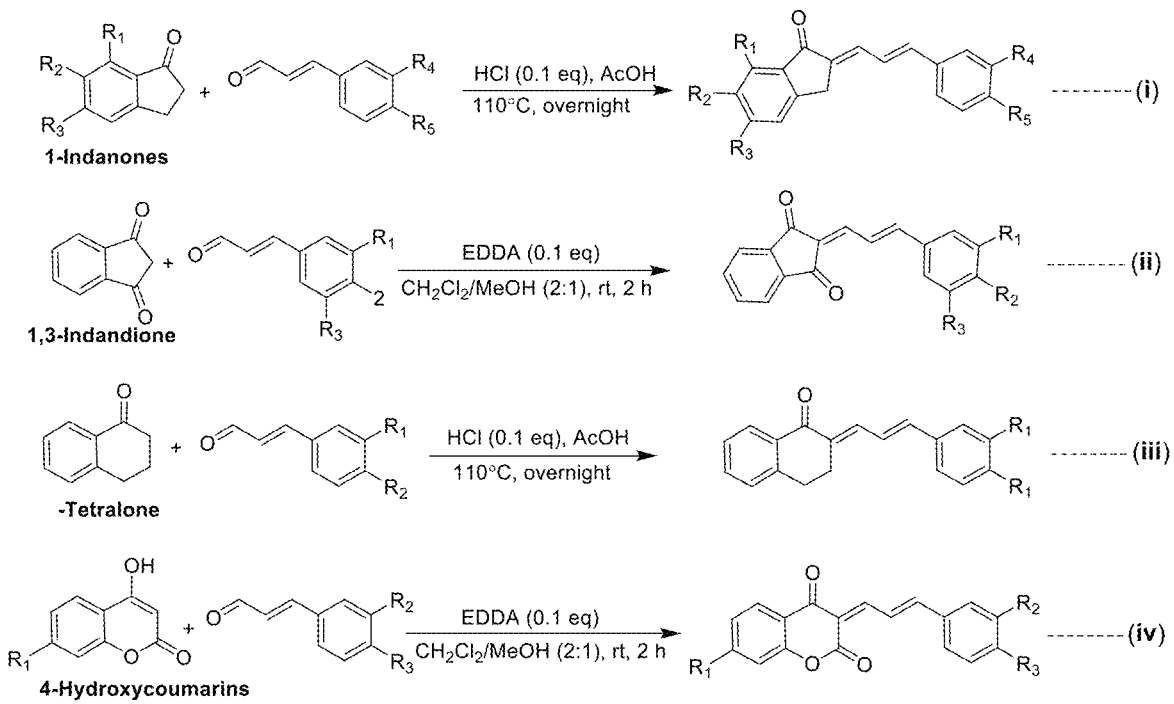
FIG. 5 provides synthetic equations to new α-syn ligands, including 1-indanonyl-, 1,3-indandionyl-, α-tetralonyl-, and 4-oxocoumarinyl-diene derivatives.

With reference to FIG. 5, a first series of derivatives in which ring A is replaced with either a 1-indanonyl-(equation i, to generate compounds 7-15, as shown in FIG. 3), 1,3-indadionyl-(equation ii, to generate compounds 16-22, as shown in FIG. 3), α-teralonyl-(equation iii, to generate compounds 23-24, as shown in FIG. 3), or coumarinyl-(equation iv, to generate compounds 25-28, as shown in FIG. 3) moieties, while maintaining the diene bridge (B), were accessed by acid or base-catalyzed aldol condensation reactions of the desired keto substrate with the corresponding cinnamaldehyde derivatives.

Thus, to a solution of aldehyde (1.0 eq) and indolinone (1.0 eq) in acetic acid (10 mL) was slowly added 37% HCl (0.5 mL). The reaction mixture was stirred at 110° C. overnight and cooled to room temperature. The cooled solvent was poured into ice water and filtered out. The solid was recrystallized with methanol.

Alternatively, to a solution of aldehyde (1.0 eq) and indolinone (1.0 eq) in dichloromethane/methanol (1:2, 10 mL) was slowly added ethylenediamine dihydrochloride (0.25 mmol). The reaction mixture was stirred at room temperature for 5 h. The solid was filtered out and recrystallized with methanol.

Particularly as it respects compound 8, (E)-2-((E)-3-(4-Hydroxy-3-methoxyphenyl)allylidene)-2,3-dihydro-1H-inden-1-one, the compound was prepared by the acidic protocol, with 1-indanone (250 mg, 1.89 mmol) and 4-hydroxy- 3-methoycinnamaldehyde (337 mg, 1.89 mmol), to afford the desired product (8) as a red solid (436 mg, 79% yield). 1H NMR (600 MHz, DMSO-d6) δ 9.52 (s, 1H), 7.74 (d, J=7.8 Hz, 1H), 7.69 (td, J1=1.2 Hz, J2=7.2 Hz, 1H), 7.64 (d, J=7.8 Hz, 1H), 7.47 (t, J=7.2 Hz, 1H), 7.29 (dt, J1=1.8 Hz, J2=10.2 Hz, 1H), 7.28 (s, 1H), 7.13 (d, J=15.6 Hz, 1H), 7.09 (dt, J1=10.2 Hz, J2=15.6 Hz, 1H), 7.06 (d, J=8.4 Hz, 1H), 6.81 (d, J=8.4 Hz, 1H), 3.93 (s, 2H), 3.86 (s, 3H); 13C NMR (150 MHz, DMSO-d6) δ 192.9, 149.6, 148.9, 148.4, 143.3, 139.3, 135.1, 134.9, 134.2, 128.4, 127.9, 127.1, 123.7, 122.6, 122.5, 116.1, 111.0, 56.2, 30.7. HRMS (ESI) calcd for C19H17O3 [M+H]+293.1172, found, 293.1171.

Figure 6:
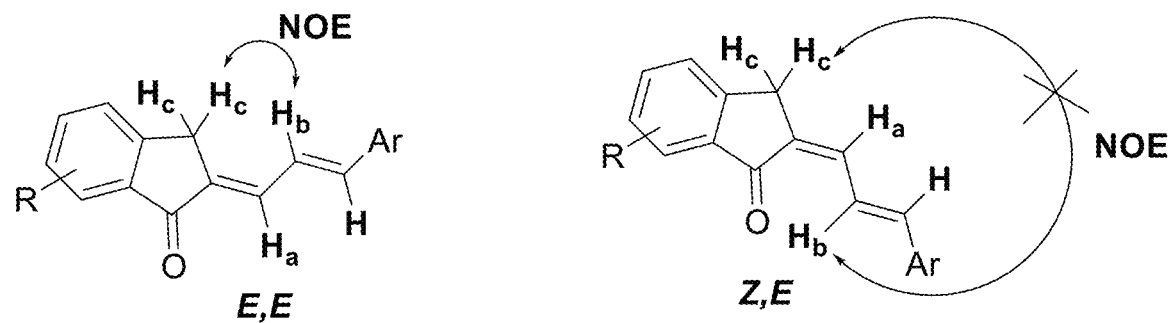
FIG. 6 provides a schematic representation of the Nuclear Overhauser Effect ("NOE") in E,E configuration of diene derivatives.

Early runs suggested that the mono-keto substrates resulted in cleaner reaction products and better yields under acidic conditions, while the di-keto substrates preferred basic conditions. Therefore, subsequent reactions involving these substrates were carried out under similar reaction conditions. Both $^1$H and $^{13}$C NMR spectra of the resulting dienes showed peaks consistent with a single product, suggesting that only one of the two possible isomers (E,E or Z,E) was formed. Further analyses of the heteronuclear multiple bond connectivity ("HMBC") and NOE spectra suggested that the isolated products had the E,E configuration, due to NOE enhancements observed between the highlighted protons (FIG. 6).

Figure 7:
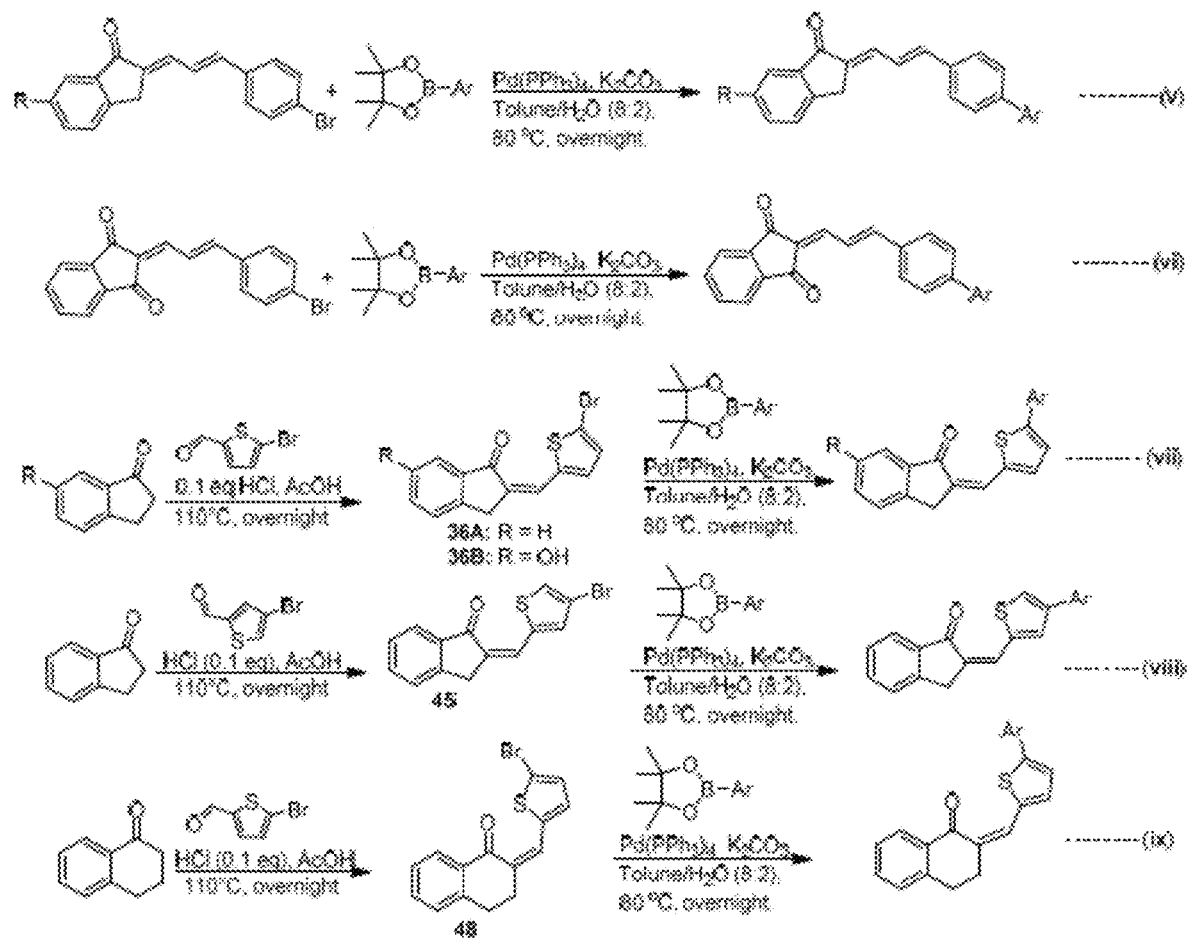
FIG. 7 provides synthetic equations to new α-syn ligands, including 1-indanonyl- and 1,3-indandionyl-diene derivatives.

Derivatives in which one of the double bonds of the bridging diene system is replaced with an electron-rich thiophene moiety to increase the electron density within the molecule were synthesized in two steps as shown in equations vii-ix (FIG. 7). First, 5-bromo-2-thiophenecarboxaldehyde was exposed to 1-indanone (or 6-hydroxyl-1-indanone) under aldol condensation reaction conditions to yield the thiobromo intermediate 36, which was exposed to a variety of arylboronic esters under Suzuki coupling reaction conditions (equation vii) to generate compounds 37-44. Similarly, other derivatives in this series were prepared from the aldol condensation of 1-indanone (equations vii and viii) and α-tetralone with 4-bromo-2-thiophenecarboxaldehyde and 5-bromo-2-thiophenecarboxaldehyde respectively, to generate the corresponding thiobromide intermediates 45 and 48. These intermediates were then exposed to different arylboronic esters to obtain compounds 46 and 47 and compounds 49-51, respectively.

More specifically, with reference to FIGS. 7 and 8, a second series of 1-indanonyl- and 1,3-indandionyl-diene derivatives was generated by appending a second ring to 1-indanonyl-diene bromides (7 and 11) and 1,3-indandionyl-diene bromide (17) via Suzuki coupling of respective arylboronic esters to generate compounds 29-35 as shown in equations v and vi. Thus, a solution of indolinone derivatives (1.0 eq), boronic derivatives (2.0 eq), and $K_2CO_3$ (1.0 eq) in 1,4-dioxane/$H_2O$ (4:1, 10 mL) was degassed by argon for 20 min, and Pd(PPh$_3$)$_4$ (0.1 eq) was added. The reaction mixture was degassed again (5 min) and stirred at 110° C. overnight. The reaction mixture was quenched with water (5 mL), and the aqueous layer was extracted with ethyl acetate (30 mL), washed with saturated NaHCO$_3$ (10 mL), and washed with brine (10 mL). The combined organic layer was dried over Na$_2$SO$_4$ and concentrated under reduced pressure. The residue was purified by column chromatography.

Figure 9:
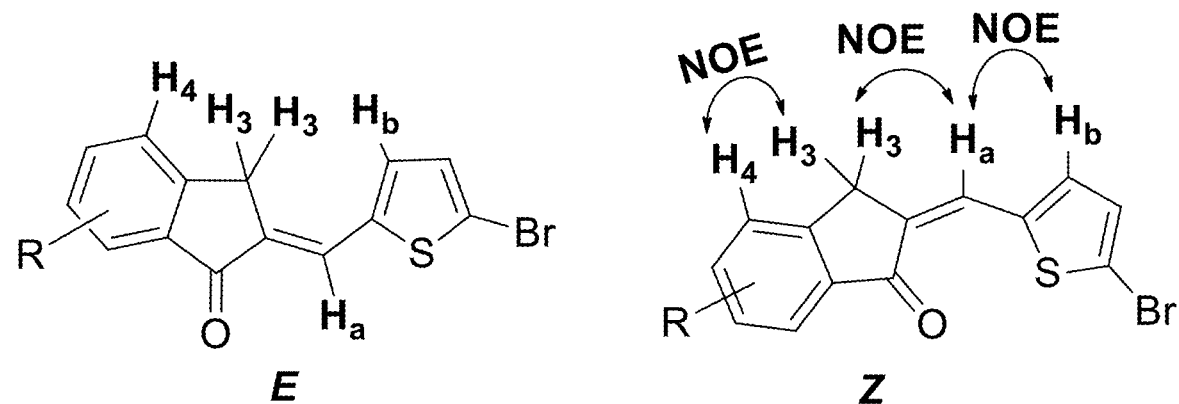
FIG. 9 provides a schematic representation of the NOE interactions in compounds 36, 45, and 48.

Analysis of NOE (FIG. 9) and HMBC spectra of compounds 36, 45, and 48 showed that the ensuing double bond from the respective aldol condensation reactions all have the Z conformation.

Figure 10:
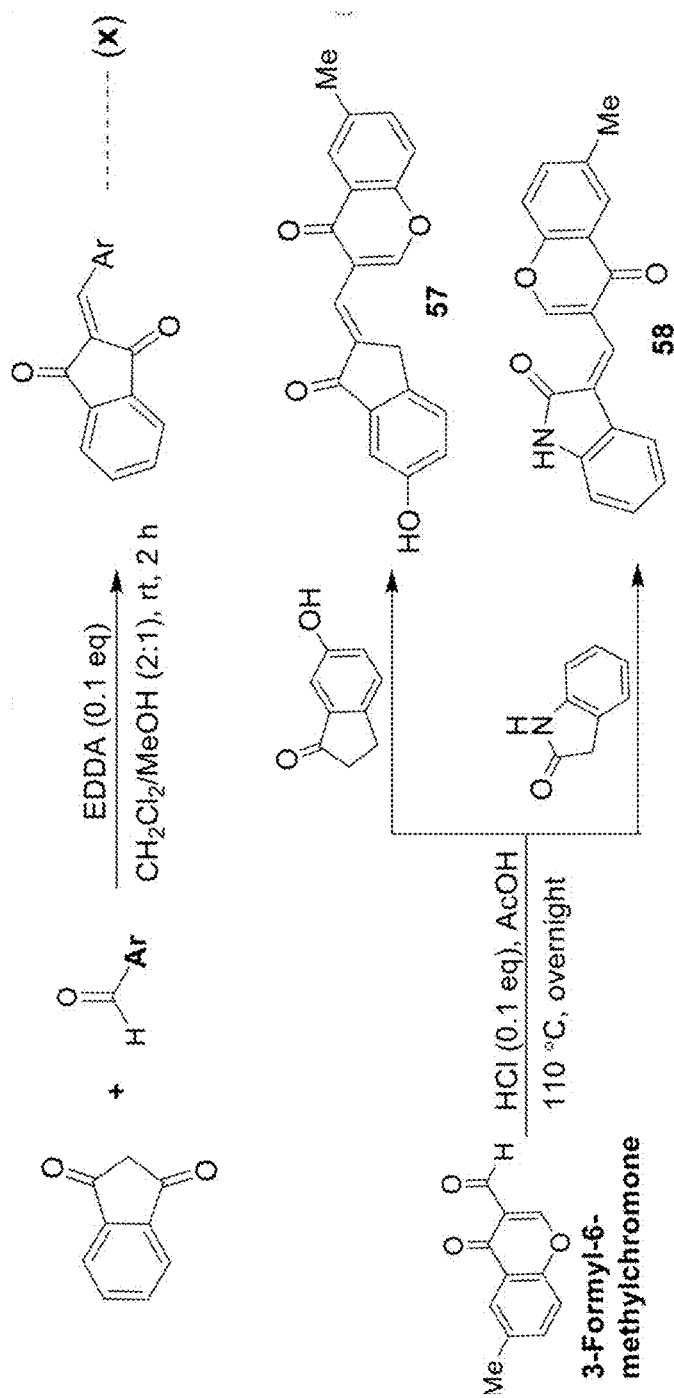
FIG. 10 provides synthetic equations to miscellaneous derivatives wherein one of the double bonds of the bridging diene is masked within a ring system to increase rigidity within the compound.
Figure 11:
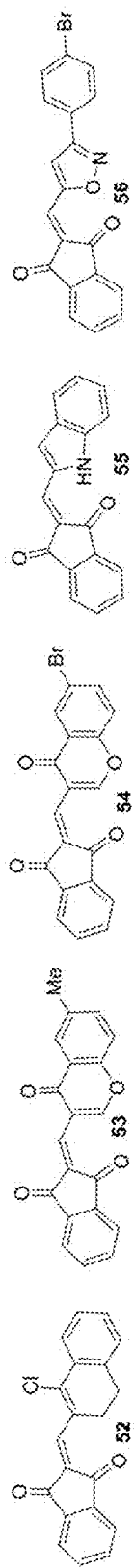
FIG. 11 provides the chemical structures of new α-syn ligands, including miscellaneous derivatives in which the second double bond of the bridging diene is masked.

Miscellaneous derivatives in which one of the double bonds of the bridging diene is masked within a ring system to increase rigidity within the molecule were accessed as shown in FIG. 10. All members of this series were accessed in a single aldol condensation reaction between the respective keto-derivatives and corresponding aldehydes. FIG. 11 provides the chemical structures of miscellaneous derivatives.

Structure elucidation for all compounds was achieved by analysis of $^1$H and $^{13}$C NMR, and high-resolution mass spectra of each individual compound. The UV/VIS absorption and emission spectra of all compounds were recorded in phosphate buffered saline ("PBS"). All compounds with fluorescence properties suitable for fluorescence microscopy studies were selected for synthetic fibril binding studies.

Example 3: Binding Affinity ($K_d$) to Synthetic α-Syn Fibrils

All synthesized compounds (except 19 and 28) showed good emission spectra in PBS (FIG. 12, Table 1). Binding affinities were determined. Binding affinity is the strength of the binding interaction between a single biomolecule and its ligand/binding partner. Binding affinity is measured and reported by the equilibrium dissociation constant ($K_d$), which is used to evaluate and rank order strengths of bimolecular interactions. The smaller the $K_d$ value, the greater the binding affinity of the ligand for its target. The larger the $K_d$ value, the more weakly the target molecule and ligand are attracted to and bind to one another.

α-Syn Fibril Formation

Fibrils were made from the peptide purchased from R-peptide (1 mg cat #S-1001-2. Mol. Wt. 14460) via the following procedure: 0.5 mg α-syn was suspended in 0.2 ml water in a centricon (10000 MWCO). To this suspension was added 0.2 mL phosphate buffer (10 mM, pH 7.5). The soluble materials were removed by spinning for 5 min in a centrifuge (18000 g/s). The process was repeated four times. After the fourth time, the peptide was transferred into a microtube (200 µl), and 2.5 µl of 300 mM MnCl (made in water) was added. The resulting mixture was stirred at 40° C. in an incubator for 5-7 days (the solution turned hazy). The fibrils formed were spun down at 21,000 g/s for 6 min. The supernatant was discarded, and the fibril pellet was resuspended in 200 µl PBS buffer (pH=7.4).

α-Syn Fibril/Ligand Binding Assay

Ligand solutions at various concentrations from 0.1 nM to 10 µM in PBS (pH=7.5, 197 µL) were added into microtubes containing α-syn fibrils (3 µL, 2.5 µM final concentration). The mixture was incubated at 37° C. for 1 h with shaking. The mixture was spun down at 21,000 g/s for 15 min to separate the fibrils. The precipitate was washed twice with Tris-HCl and resuspended in 200 µL buffer. Fluorescence was measured in a SpectraMax-384 plate reader using excitation and emission maxima of the molecule. All data points were performed in triplicate. The $K_d$ and the maximal number of binding sites (Bmax) values were determined by fitting the data to the equation Y=Bmax×X/(X+$K_d$) by nonlinear regression using MATLAB software (R2019B).

All compounds that showed $K_d$ values ≥2 µM (compounds 7, 11, 16-18, 28, 52-54, and 56) were considered insufficient binders and reported as no binding ("NB").

In general, the 1-indanon-diene derivatives appeared to be better binders than the corresponding 1,3-indandion-diene, as exemplified by 8 vs 20 and 10 vs 22. Any aromatic substitution (activating, 13 or deactivating, 14 and 15) on the 1-indanon-diene moiety reduced binding affinity compared to the non-substituted derivatives 10 and 8 respectively. The α-tetralon-diene and coumarin-diene derivatives all showed inferior binding relative to the corresponding 1-indanon-diene and 1,3-indandion-diene derivatives as exemplified by 8, 20, 23, and 25. Apart from compound 32 with a $K_d$ of 18.8 nM, appending a second ring to the second aromatic group (C) did not improve the binding affinity of either the 1-indanon-diene or the 1,3-indandion-diene system. Similarly, replacing one of the double bonds in the diene bridge with an electron-rich thiopenyl moiety (compounds 8 vs 39) had no positive impact on the binding affinity of the ligands to α-syn fibrils, other than some modest $K_d$ values (compounds 37, 39, and 42). Rendering the system more rigid by masking the second double bond of the bridging diene in a fused ring with C (compounds 52-58) led to low and no-binding.

Figure 13:
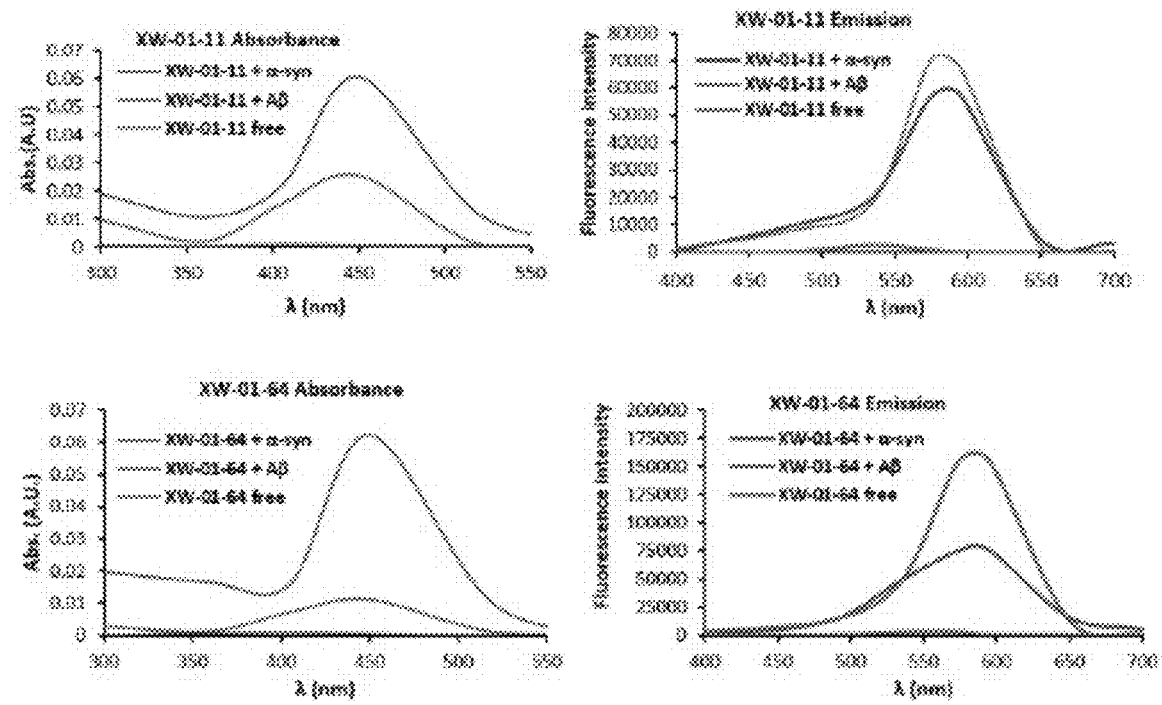
FIG. 13 shows representative absorption/emission spectra of free ligands vs. bound to α-syn or Aβ fibrils using ligands 8 (XW-01-11) and 32 (XW-01-64).

Example 4: Fluorescence Properties and Ligand Binding Selectivity to α-Syn Versus Aβ Fibrils Although α-syn aggregates represent the most dominant misfolded protein aggregates encountered in PD and other synucleinopathies, several studies suggest that Aβ and tau aggregates often overlap with α-syn. Potential α-syn agents for in vivo applications must be both highly sensitive and selective (especially versus Aβ) to minimize false positives in such cases. The preliminary α-syn fibril binding studies of 11 ligands showed high to moderate affinity ($K_d$≤100 nM). The fluorescence properties and binding affinity of these ligands to α-syn compared to Aβ fibrils were further evaluated. The absorption and emission maxima and the fluorescence quantum yields of the free ligand and in the presence of either α-syn or Aβ fibrils were determined. As exemplified by data for ligands 8 (XW-01-11) and 32 (XW-01-64) (FIG. 13), all of the ligands show minimal fluorescence at concentrations ≤0.5 μM in aqueous media, but this increased remarkably upon the addition of either α-syn or Aβ fibrils.

The increase in fluorescence is accompanied by a bathochromic shift in both absorbance and emission maxima from free molecule to ligand-fibril complex, accompanied by an 8- to 15-fold increase in fluorescence quantum yield upon ligand binding to α-syn fibrils and an additional 2- to 3-fold increase upon binding to Aβ fibrils (FIG. 14, Table 2).

The observed bathochromic shifts in fluorescence and emission maxima, the increase in fluorescence, and fluorescence quantum yields upon fibril binding by these ligands are consistent with other observations of β-sheet binding ligands.

The binding affinities for Aβ fibrils were evaluated in saturation binding assays.

Aβ Fibrils Formation

β-Amyloid (1-40) peptide was purchased from R-Peptide (Bogart, Ga.). The fibrils were prepared following the protocol outlined by Eric et al. (PLoS One, 2012, 7(10), e48515). Aβ (1-40) was dissolved in PBS, pH 7.4 to a final concentration of 433 μg/ml (100 μM). The solution was stirred using a magnetic stir bar at 700 rpm for 4 d at room temperature to drive the formation of fibrils. The stock solution was aliquoted and stored at −80° C. for future use. The stock solutions were stirred thoroughly before removing aliquots for binding assays, to maintain a homogenous suspension of fibrils.

Aβ Fibril/Ligand Binding Assay

Ligand solutions at various concentrations from 1 nM to 100 μM in PBS (pH=7.5, 180 μL) were added into microtubes containing β-amyloid fibrils (20 μL, 10 μM final concentration). The mixture was incubated at 37° C. for 1 h with shaking. The mixture was spun down at 21,000 g/s for 12 min to separate the fibrils. The precipitate was washed twice with Tris-HCl and resuspended in 200 μL buffer. Fluorescence was measured in a SpectraMax-384 plate reader using excitation and emission maxima of the molecule. All data points were performed in triplicate. The $K_d$ and the maximal number of binding sites (Bmax) values were determined by fitting the data to the equation $Y=Bmax \times X/(X+K_d)$ by nonlinear regression using MATLAB software (R2019B).

The results (FIG. 15, Table 3) show that apart from compound 29, all the other compounds have triple digit dissociation constants in the nanomolar range to Aβ fibrils, compared to the double digits to α-syn fibrils. Comparison of the $K_d$ values of each compound between the two protein aggregates suggests that compound 8, having the highest affinity ($K_d$=9.7 nM), has a 14.4-fold selectivity versus Aβ. Compound 32, a slightly more moderate α-syn binder ($K_d$=18.8 nM), has a 26-fold selectivity versus Aβ. Compound 37, also a moderate α-syn binder ($K_d$=34.9 nM), has an 11.2-fold selectivity versus Aβ.

Example 5: Fluorescent Human PD and AD Tissue Staining

Figure 16:
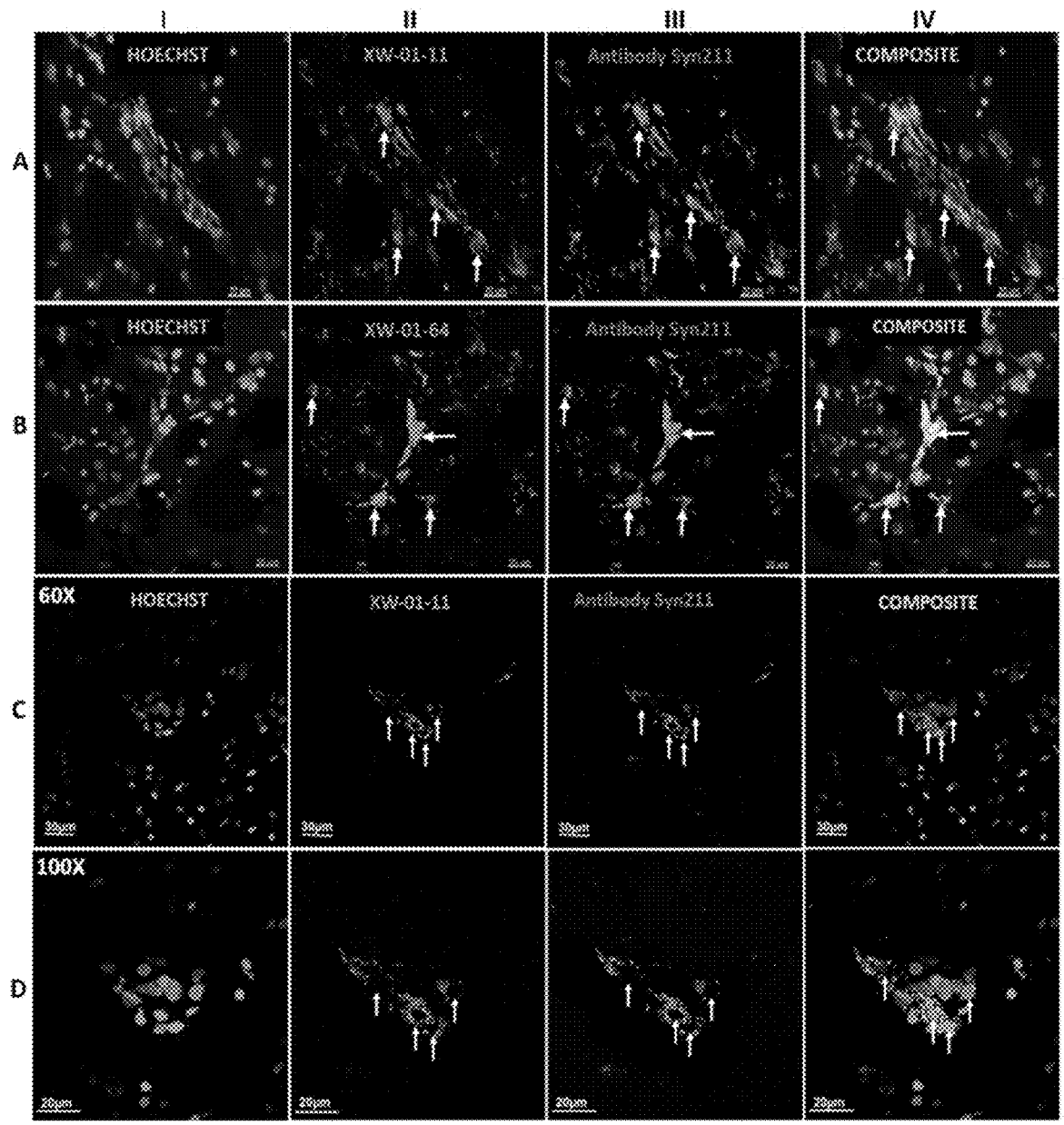
FIG. 16 shows confocal microscopy images of PD brain tissue sections co-stained with an anti-α-syn antibody and ligands 8 (XW-01-11) and 32 (XW-01-64).

Given the adequate fluorescent properties, high affinity, and selectivity toward α-syn aggregates, ligands 8, 32, and 37, with α-syn versus Aβ selectivities of 14.4-, 26-, and 11.2-fold, respectively, were further evaluated in in vitro fluorescent staining of neuropathologically verified post-mortem brain samples of human PD and AD patients. Sections from the pons and frontal-cortex of the PD brain were permeabilized and treated sequentially with antibody [Anti-alpha-Synuclein (aa 121-125) Antibody, clone Syn 211] and 1 μM solution of each compound and visualized by confocal microscopy. FIG. 16, column I, shows fluorescence HOECHST stain highlighting cell nuclei, thereby providing a perspective of cell bodies within the tissue. Column II depicts ligand fluorescence. Column III depicts fluorescence from the antibody. Column IV is a composite image created by merging the first three images. Row A shows images obtained from a section of the frontal cortex from the PD brain, treated with compound 8 (XW-01-11). As can be seen in the image, the ligand avidly labels Lewy pathology within the tissue. The pattern and labeling intensity appear similar in the antibody channel. The composite image shows co-localization of the ligand and antibody signals, confirming that they bind the same pathology. Similarly, a section treated with ligand 32 (XW-01-64), row B, shows avid labeling of Lewy pathology by the ligand, which is corroborated by the staining pattern and intensity of the antibody. As observed with ligand 8, a composite imaged from merging the ligand 32 and the antibody images also shows co-localization of both signals confirming the efficiency of these ligands in labeling Lewy pathology in post-mortem human PD brain sections. In up close Z-stacked images of the treated tissue (Row C), the pathology appears to surround dark holes (arrows) in the ligand and antibody channels. A composite image created by merging nuclei stain, ligand, and antibody signals shows that dark spots in the ligand and antibody channels are actually the spots occupied by the nuclei that are more prominent at high magnification (Row D). The close proximity and location of the nuclei suggest that, as expected, the observed pathologies are cytoplasmic inclusions and not extracellular aggregates.

Figure 17:
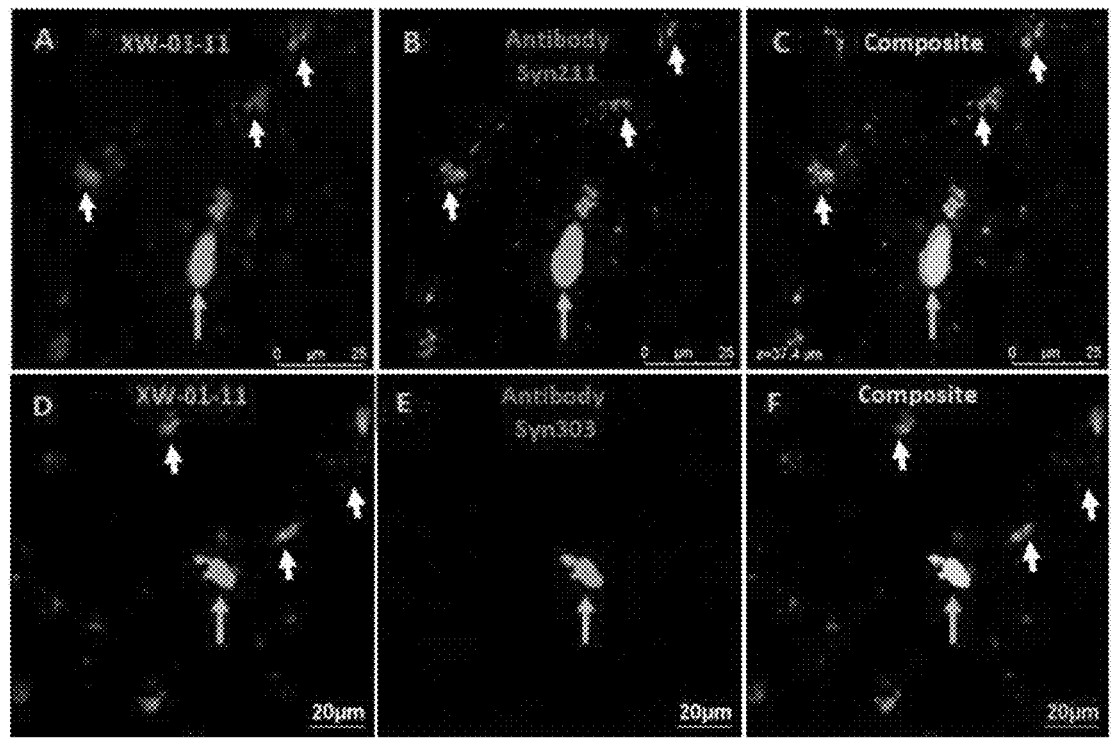
FIG. 17 shows confocal microscopy images of PD brain tissue sections co-stained with anti-α-syn antibodies and ligand 8 (XW-01-11).

To further characterize the sites labeled by the ligands and antibody Syn211 tissue staining experiments, contiguous cortical sections were treated with compound 8 and then either Syn211 or Syn303. As expected, the sections treated with compound 8 and Syn211 (FIG. 17, first row) show identical ligand and antibody labeling patterns that colocalize in the composite image. Both the ligand and antibody appear to label all forms of pathology present on the tissue. On the other hand, tissue sections treated with the ligand and antibody Syn303 (FIG. 17, second row) show effective labeling of both small neurites (upper arrows) in the ligand channel, but only mature Lewy bodies in the antibody channel (lower arrow). These findings suggest that the labeled pathology is α-syn, and that the ligand labels all conformations of the pathology.

Figure 18:
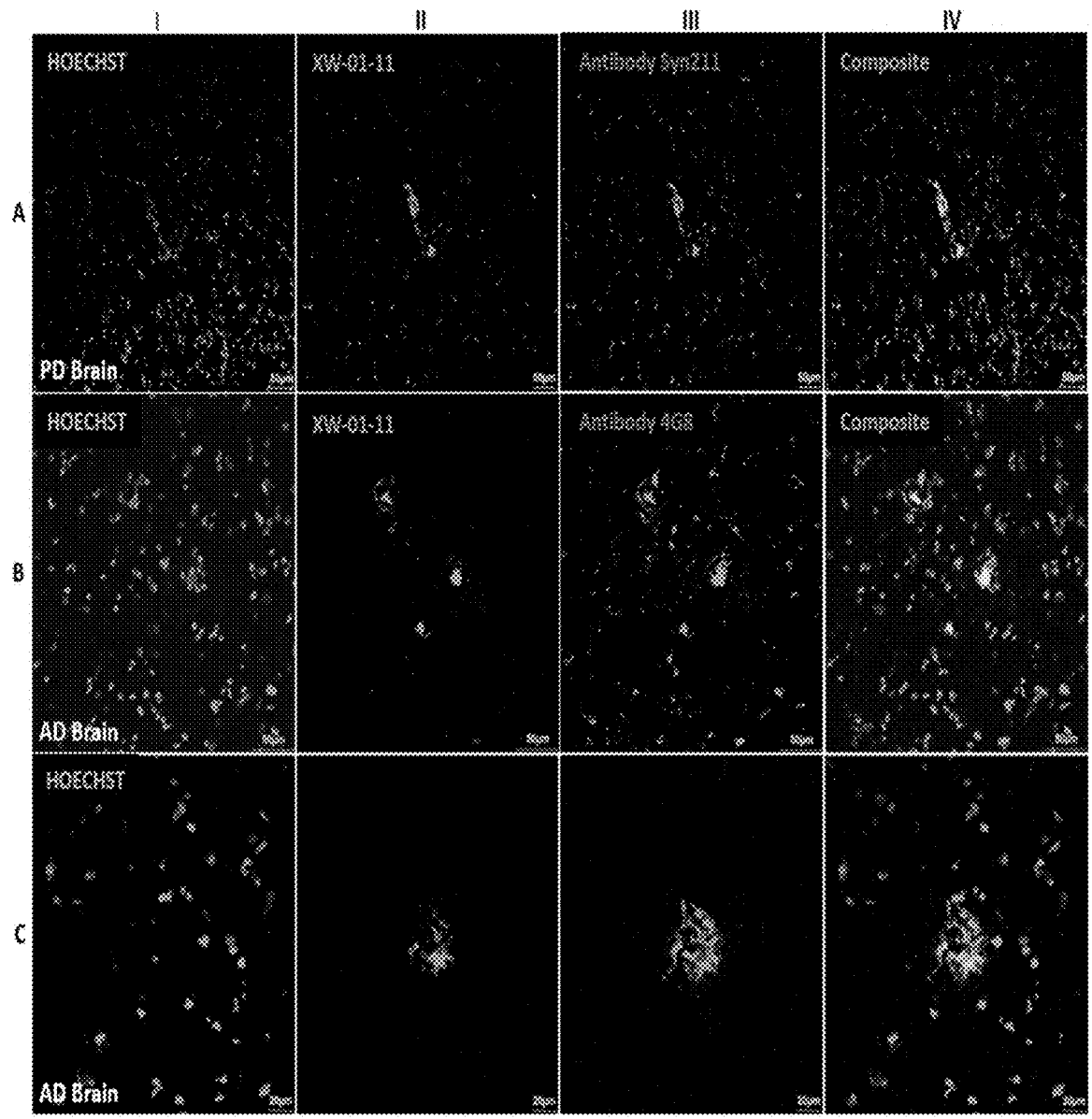
FIG. 18 shows comparative confocal microscopy images of PD and AD brain tissue sections co-stained with ligand 8 (XW-01-11) and respective anti-α-syn versus anti-Aβ antibodies.

To assess the observed selectivity in α-syn versus Aβ fibril binding on aggregates in human tissue, equimolar concentrations of ligands 8, 32, and 37 were further evaluated on PD tissue as described above, alongside cortical sections from neuropathologically verified post-mortem brain samples of AD patients. FIG. 18 shows data from the top binder (compound 8), which has a selectivity of 14.4-fold for α-syn vs Aβ. As can be observed in Row A, the PD tissue shows avid labeling of both large and fine deposits of the pathology (column II). A similar labeling pattern and efficiency are observed in the antibody channel (column III). A composite image generated by merging both signals with the HOECHST signal (column IV) shows co-localization of the ligand and antibody signals. Unlike the PD tissue, fluorescent images from the AD tissue (Row B) show mostly dense core Aβ plaques in the ligand channel (column II), but not the finer aggregates composed of diffuse plaques. The antibody, anti-β-Amyloid, 17-24 Antibody (4G8), highlights both dense core and diffuse Aβ pathology (column III). A composite image generated by merging both signals with the HOECHST signal shows overlap of the ligand and antibody signals from the dense core plaques (column IV). This data suggests that the ligand labels fibrillar α-syn with greater efficiency than fibrillar Aβ. High magnification images from the treated AD tissue (Row C) show that, as expected, the observed Aβ pathology is extracellular, unlike the intracellular Lewy pathology observed in the PD tissue.

Human Tissue Acquisition

Human PD brain tissue and AD brain tissue were obtained from the NIH Neurobiobank.

Labeling of α-Syn Pathology in Human PD Brain Tissue

Midbrain tissue (Frontal cortex 5469) was embedded with Tissue-Tek O.C.T. Compound and kept in liquid nitrogen for 30 min. The embedded tissue was sliced into 30 μm thick sections with Lecia Biosystems Cryostats under –20° C. and mounted onto Precleaned Microscope Slides. The section was washed with 1× PBST two times and loaded with 10% formalin solution for 20 min. The section was washed with 1× PBS three times and permeabilized with 0.1% Triton-X 100 for 10 min. The section was washed with 1× PBS two times and incubated with 2% normal Donkey serum at room temperature for 1 h. The section was incubated with Anti-alpha-Synuclein (aa 121-125) Antibody, clone Syn 211 (Ascites free) (1:1000 in 1% Donkey serum) overnight at 4° C. and washed with 1× PBS three times. The section was incubated for 2 h at room temperature with a fluorescent secondary antibody labeled with Alexa Fluor 488 (1:200 in PBS). The section was washed with 1× PBST three times and treated with the compound to be tested. Each tissue section was incubated at room temperature for 30 min with 5 μM of test compound dissolved in PBS. The section was washed with 1× PBST three times and loaded with True-Black Lipofuscin Autofluorescence Quencher (1:20 in ethanol) for 2 min. The section was washed with 1× PBS three times and coverslipped. The tissue was imaged with Lecia DMi8 Motorized Fluorescence Microscope using standard excitation/emission filters for Alexa Fluor 488 or Alexa Fluor 647.

Staining of β-Amyloid Plaques in Human AD Brain Tissue

Midbrain tissue (Frontal cortex 5590) was embedded with Tissue-Tek O.C.T. Compound and kept in liquid nitrogen for 30 mins. The embedded tissue was sliced into 30 μm thick sections with Lecia Biosystems Cryostats under –20° C. and mounted onto Precleaned Microscope Slides. The section was washed with 1× PBST two times and then loaded into 10% formalin solution for 20 mins. The section was washed with 1× PBS three times and permeabilized with 0.1% Triton-X 100 for 10 min. The section was washed with 1× PBS two times and incubated with 2% normal Donkey serum at room temperature for 1 h. The section was incubated with Purified anti-β-Amyloid, 17-24 Antibody (4G8) (1:500 in 1% Donkey serum) overnight at 4° C. and washed with 1× PBS three times. The section was incubated for 2 h at room temperature with a fluorescent secondary antibody labeled with Alexa Fluor 488 (1:200 in PBS). The section was washed with 1× PBST three times and treated with the compound to be tested. Each tissue section was incubated at room temperature for 30 min with 5 μM of test compound dissolved in PBS. The section was washed with 1× PBST three times and loaded with TrueBlack Linpofuscin Autofluorescence Quencher (1:20 in ethanol) for 2 min. The section was washed with 1× PBS three times and coverslipped. The tissue was imaged with Lecia DMi8 Motorized Fluorescence Microscope using standard excitation/emission filters for Alexa Fluor 488 or Alexa Fluor 647.

Human Brain Tissue HRP-DAB Staining

Midbrain tissue (Frontal cortex 5469 or Frontal cortex 5590) was fixed with Tissue-Tek O.C.T. Compound and kept in liquid nitrogen for 30 mins. The freezer tissue was sliced into 30 μm thick sections with Lecia Biosystems Cryostats under –20° C. and mounted onto Precleaned Microscope Slides. The section was washed with 1× PBST two times and loaded with 10% formalin solution for 20 min. The section was washed with 1× PBS three times and 50 μl of peroxide Block was applied to each section and incubated for 10 min at room temperature. The section was washed with 1× PBS two times and incubated with 2% normal Donkey serum at room temperature for 1 h. The section was incubated with Anti-alpha-Synuclein (aa 121-125) Antibody, clone Syn 211 (Ascites free) (1:1000 in 1% Donkey serum) or Purified anti-β-Amyloid, 17-24 Antibody (4G8) (1:500 in 1% Donkey serum) overnight at 4° C. and washed with 1× PBS three times. The section was incubated with biotinylated secondary antibody for 2 h at room temperature and washed with 1× PBST three times. The section was incubated with Streptavidin/HRP label for 30 min and washed with 1× PBST three times. The section was incubated with distilled water for 10 min and incubated with DAB Chromagen (Combine 50 μL of DAB Chromagen to 1 ml of DAB substrate). The section was washed with distilled water three times and dehydrated through grades of alcohol for 10 min. Finally, the section was washed with xylene to coverslip, stored at room temperature for 2 days, and imaged with bright field microscope.

Example 6: Synthesis of DSPE-PEG3400-XW-01-11 Conjugate

Figure 19:
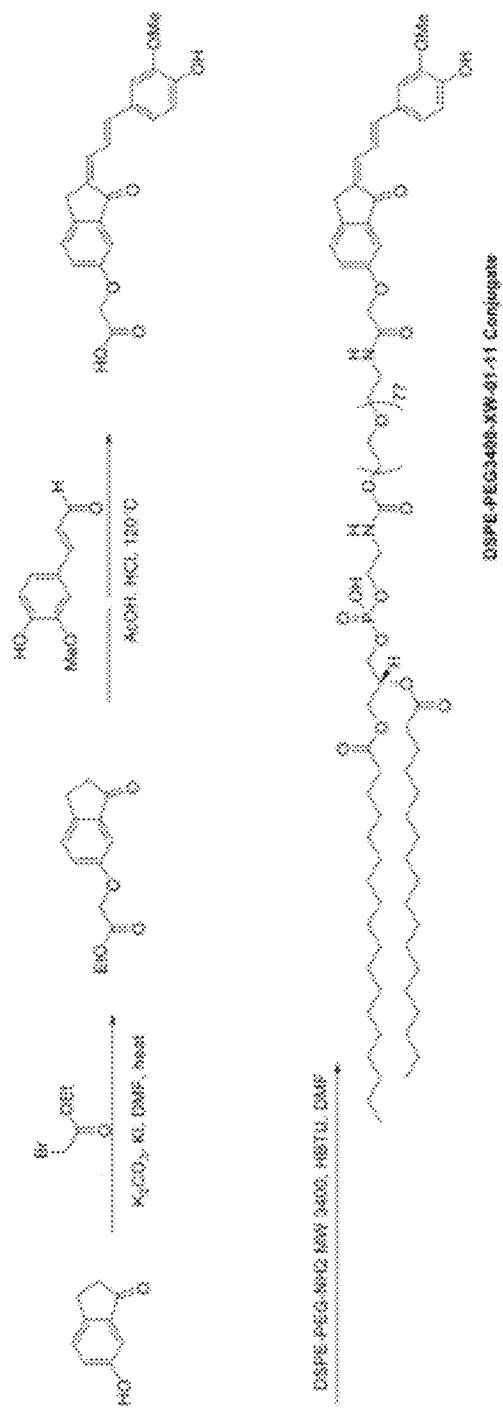
FIG. 19 shows an example synthetic scheme for the preparation of the DSPE-PEG3400-XW-01-11 Conjugate.

With reference to FIG. 19, ethyl bromoacetate (2.3 g, 13.5 mmol) was added in one portion to a solution of 6-hydroxy-1-indanone (1.0 g, 6.8 mmol), $K_2CO_3$ (2.8 g, 20.2 mmol), and KI (112 mg, 0.7 mmol) in DMF (10 mL). The reaction mixture was stirred at 90° C. overnight. At this point, TLC (silica, 1:3 EtOAc-hexanes) showed the reaction was complete. The reaction mixture was cooled to room temperature, filtered through a pad of celite using ethyl acetate (50 mL) as the eluent, and the filtrate was concentrated. The residue was purified by column chromatography to afford the desired product (1.4 g, 90%) as a white solid. $^1$H NMR (600 MHz, $CDCl_3$) δ 7.38 (d, J=8.4 Hz, 1H), 7.26 (dd, $J_1$=2.4 Hz, $J_2$=8.4 Hz, 1H), 7.10 (d, J=2.5 Hz, 1H), 4.64 (s, 2H), 4.26 (q, J=7.8 Hz, 2H), 3.06 (t, J=6.0 Hz, 2H), 2.69 (t, J=6.0 Hz, 2H), 1.29 (t, J=7.8 Hz, 3H); $^{13}$C NMR (150 MHz, $CDCl_3$) δ 206.7, 168.4, 157.6, 148.9, 138.2, 127.7, 124.4, 105.8, 65.3, 61.5, 36.9, 25.1, 14.1.

37% HCl (0.2 mL) was slowly added to the product (700 mg, 3.0 mmol) and a solution of 4-hydroxy-3-methoxycinnamaldehyde (588 mg, 3.3 mmol) in acetic acid (10 mL). The reaction mixture was stirred at 120° C. overnight and cooled to room temperature. The cooled solvent was poured into ice water and filtered out. The solid was recrystallized in methanol to afford the desired product (768 mg, 70%) as a brown solid. $^1$H NMR (600 MHz, DMSO-$d_6$) δ 13.09 (s, 1H), 9.52 (s, 1H), 7.55 (d, J=8.4 Hz, 1H), 7.32-7.24 (m, 3H), 7.13 (dd, $J_1$=6.0 Hz, $J_2$=9.0 Hz, 1H), 7.08 (d, J=5.4 Hz, 1H), 7.06 (td, $J_1$=3.0 Hz, $J_2$=7.8 Hz, 1H), 6.81 (d, J=8.4 Hz, 1H), 4.79 (s, 2H), 3.85 (s, 3H), 3.84 (s, 2H); $^{13}$C NMR (150 MHz, DMSO-$d_6$) δ 192.7, 170.6, 148.4, 142.6, 140.4, 135.8, 134.2, 127.9, 123.7, 122.4, 106.3, 65.3, 56.2, 29.9.

To the product (120 mg, 0.3 mmol) and a solution of DSPE-PEG3400-$NH_2$ (500 mg, 0.1 mmol) in dry DMF (8 mL) was added HSTU (160 mg, 0.4 mmol). The reaction mixture was stirred at room temperature for two days and concentrated under reduced pressure. The residue was diluted with methanol/water mixture (1:1, 8 ml), loaded into a 2000 MWCO dialysis cassette, dialyzed against IVIES buffer (10 mM, 2×5 liters) for 8 hours, and dialyzed against water (3×5 liters) for 2 days. The water was removed by freeze drying to obtain DSPE-PEG3400-XW-01-11 (242 mg, 48%) as a yellow solid. $^1$H NMR (600 MHz, $CDCl_3$) δ 7.45 (d, J=8.4 Hz, 1H), 7.23 (dd, $J_1$=2.4 Hz, $J_2$=5.6 Hz, 1H), 7.19-7.17 (m, 2H), 7.15 (d, J=2.4 Hz, 1H), 7.02-6.99 (m, 3H), 6.78 (dd, $J_1$=8.4 Hz, $J_2$=10.8 Hz, 1H), 5.09 (brs, 1H), 4.48 (s, 2H), 4.30 (dd, $J_1$=2.4 Hz, $J_2$=12.0 Hz, 1H), 4.12-4.06 (m, 2H), 4.01 (t, J=4.2 Hz, 2H), 3.98 (brs, 2H), 3.81-3.77 (m, 5H), 3.73 (s, 2H), 3.49 (dd, $J_1$=2.4 Hz, $J_2$=7.8 Hz, 2H), 3.48-3.46 (m, 3H), 3.35-3.32 (m, 4H), 3.20-3.18 (m, 2H), 2.21-2.18 (m, 4H), 1.93-1.92 (m, 4H), 1.50-1.47 (m, 4H), 0.761 (t, J=6.0 Hz, 6H); HRMS (MALDI) calcd for $C_{219}H_{410}N_2O_{92}P$ $[M+H]^+$ 4571.7203, found, 4571.7069.

Example 7: Fabrication of Compound 8 (XW-01-11)-Labeled Liposomes

A lipid mixture comprising HSPC:DSPE-mPEG2000: Chol:Gd-DOTA-DSPE:DSPE-PEG3400-XW-01-11 in a molar ratio (%) of 32:2.5:40:25:0.5 was dissolved in ethanol (600 μL) at 60-65° C. For these experiments, DHPE-Rhodamine dissolved in ethanol (1 mg in 200 μL) was added, and the ensuing solution hydrated with histidine buffered saline (HBS) (10 mM Histidine, 140 mM NaCl, ~pH 7.6) at 60-65° C. for 45 mins. The hydrated lipid solution was extruded sequentially through 400 nm (5 passes) followed by 200 nm (8 passes) Nucleopore membranes at 60-65° C. using a high-pressure extruder (Northern Lipids, Vancouver, BC, Canada) to form liposomes of desired size (Dynamic Light Scattering (DLS) instrument (Brookhaven Instruments Corp., Holtsville, N.Y., USA). The liposomal suspension was dialyzed against Histidine-buffered saline (HBS) using 300 kDa molecular weight cutoff membranes (Spectrum Laboratories Inc., CA, USA,) to remove un-encapsulated materials. Control liposomes (untargeted liposomes) were prepared using the same protocol, but the DSPE-PEG3400-XW-01-11 fraction was replaced with mPEG2000.

Figure 20:
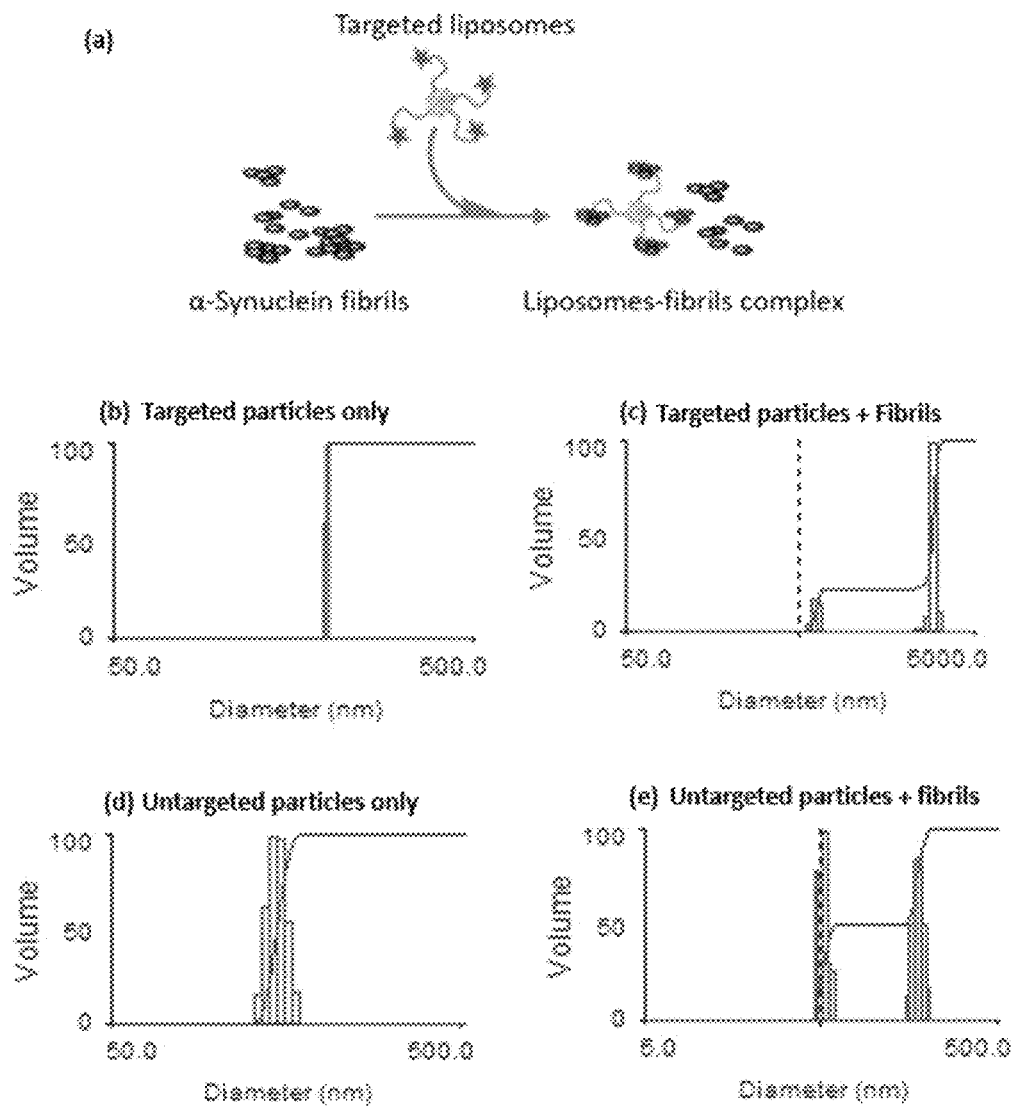
FIG. 20 shows Dynamic Light Scattering ("DLS") graphs for ligand 8 (XW-01-11) labeled liposome nanoparticles vs. control liposomes when incubated with α-syn fibrils.

Example 8: In Vitro Evaluation of Binding of Compound 8 (XW-01-11) Targeted Liposomes to α-Syn Fibrils FIG. 20 shows: (a) a cartoon depicting the reaction between the targeted liposomes of the present invention and α-syn fibrils; (b) a DLS graph showing that a solution of the ligand 8 (XW-01-11) labeled liposomes prepared in Example 7 has a mean hydrodynamic diameter of 194 nm; (c) a DLS graph showing a large increase in hydrodynamic diameter (2346 nm) after incubation of the Example 7 targeted liposomes with 1 nM α-syn fibrils for 1.5 h, which is attributed to formation of agglomerates between the nanoparticles and fibrils, held together by the high affinity of XW-01-11 to the fibrils; (d) a DLS graph showing that an example solution of untargeted nanoparticles (that is, the DSPE-PEG3400-XW-01-11 fraction was replaced with mPEG2000) has a mean hydrodynamic diameter of 169 nm; (e) a DLS graph showing that incubation of the example solution of untargeted nanoparticles with 1 nM α-syn fibrils for 1.5 h does not yield any particles with hydrodynamic diameter >500 nm, indicating the absence of interaction between untargeted nanoparticles and α-syn fibrils.

Figure 21:
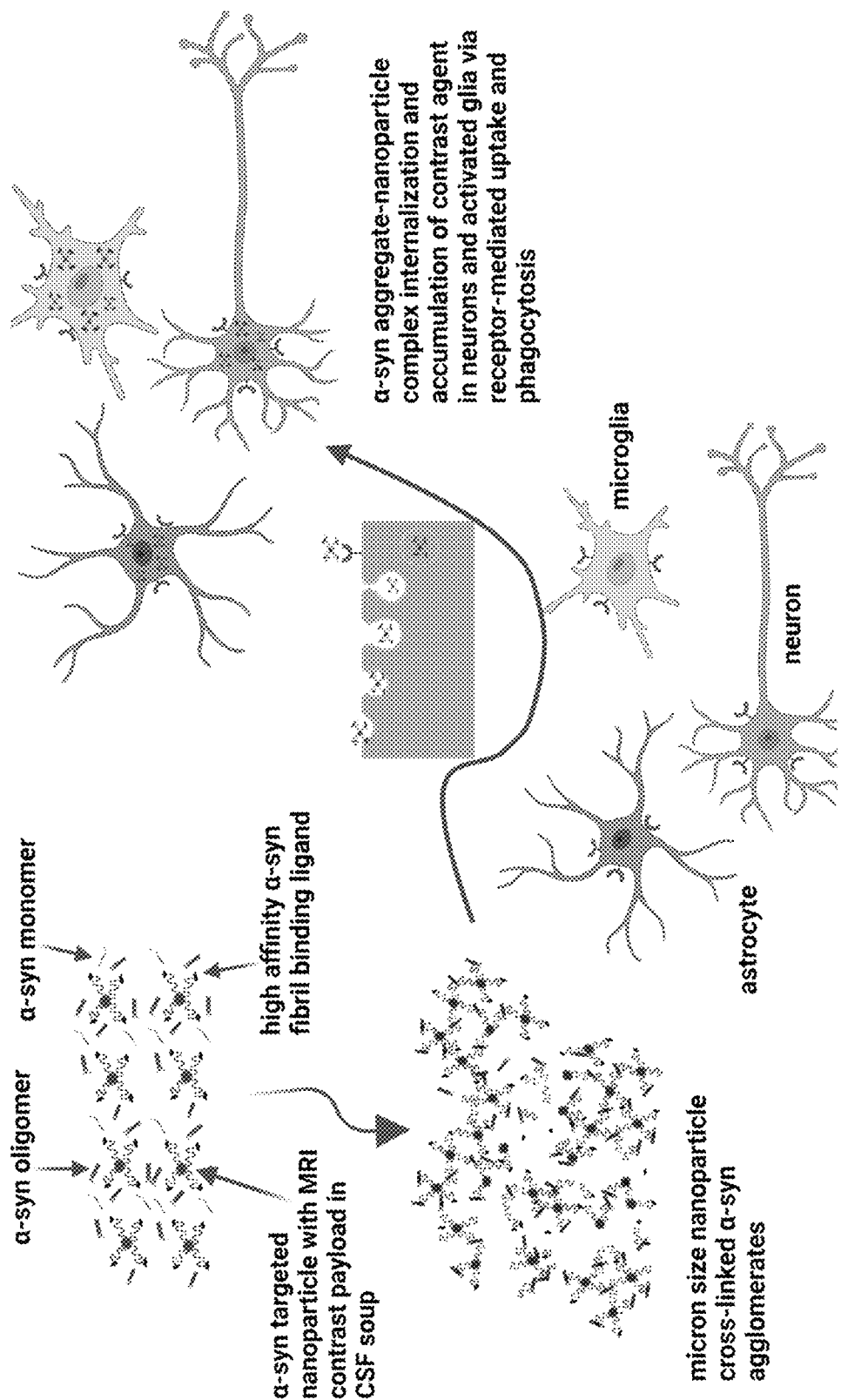
FIG. 21 is a schematic showing how the targeted nanoparticles bind and cross-link α-syn fibrils into micron size agglomerates, making them better substrates for cellular uptake by phagocytosis.

Example 9: In Vitro Cellular Uptake of Agglomerates of XW-01-11 Labeled Liposome Nanoparticles and α-Syn Fibrils Agglomerate formation was found to accelerate cellular uptake of fibrils, according to the hypothesis depicted schematically in FIG. 21. Three different cell lines, HMC-3 (microglia cell line), SH-SY5Y (neuronal cell line), and T98G cells (astroglia cell line), were used for the cell uptake studies. For these experiments, all nanoparticle formulations included a Rhodamine B label, which served as a marker for particle location in confocal microscopy experiments. The test sample included cells incubated with a mixture of the targeted nanoparticles and α-syn fibrils. Controls included cells incubated with the nanoparticles but no α-syn fibrils, cells incubated with just α-syn fibrils but no nanoparticles, and cells incubated with nontargeted nanoparticles and α-syn fibrils. As shown by data from HMC-3 cells (FIG. 22) and SH-SY5Y (FIG. 23), within 1.5 hours of incubation, test samples begin showing significant cytosolic signal (Rhodamine B), indicative of uptake of the targeted nanoparticle-fibril complex but nothing significant in the controls. FIG. 24 shows the time dependence of agglomerate/particle uptake, wherein cells incubated with fibrils and targeted nanoparticles demonstrated more rapid particle uptake compared to controls in which cells were incubated with fibrils and nontargeted particles.

Figure 22:
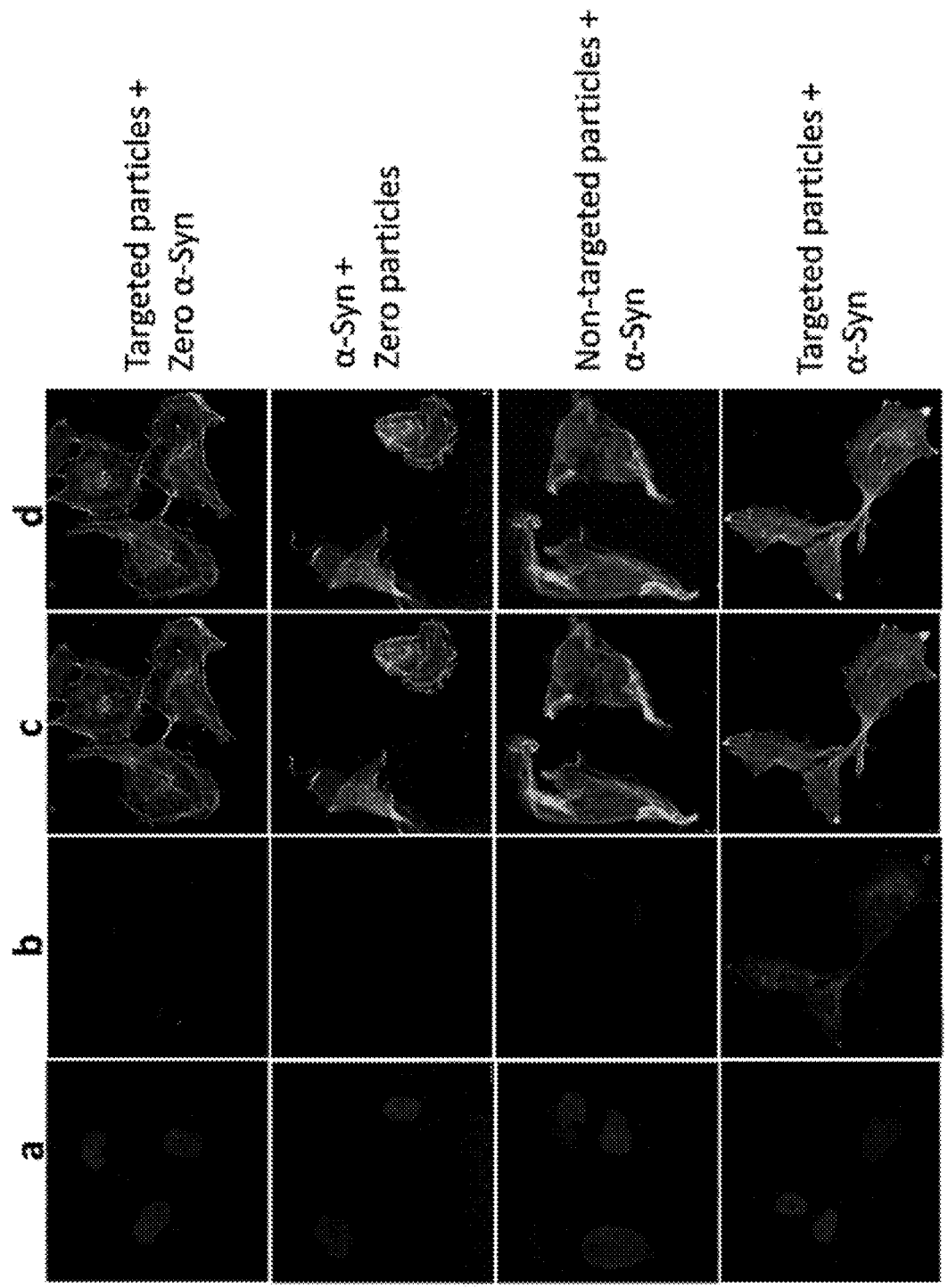
FIG. 22 shows confocal microscopy images of nanoparticle-fibril aggregate uptake within 1.5 hours in HMC-3 cells (microglia cell line) incubated with targeted nanoparticles and fibrils versus controls.

More particularly, FIG. 22 shows confocal microscopy images of nanoparticle-fibril aggregate uptake within 1.5 hours in HMC-3 cells (microglia cell line) incubated with ligand 8 (XW-01-11) labeled liposome nanoparticles and fibrils versus controls. Column (a) shows a nuclear stain that indicates the presence of cells in all slides; column (b) shows a rhodamine B signal indicative of the location of the nanoparticles and is conspicuous in the slide with cells treated with targeted nanoparticles; column (c) shows a cytoskeleton stain that maps out cell boundaries in all slides; and column (d) shows a composite of all three images, suggesting that the Rhodamine B signal on the test slide is cytosolic, confirming accelerated uptake of nanoparticle-fibril aggregate.

Figure 23:
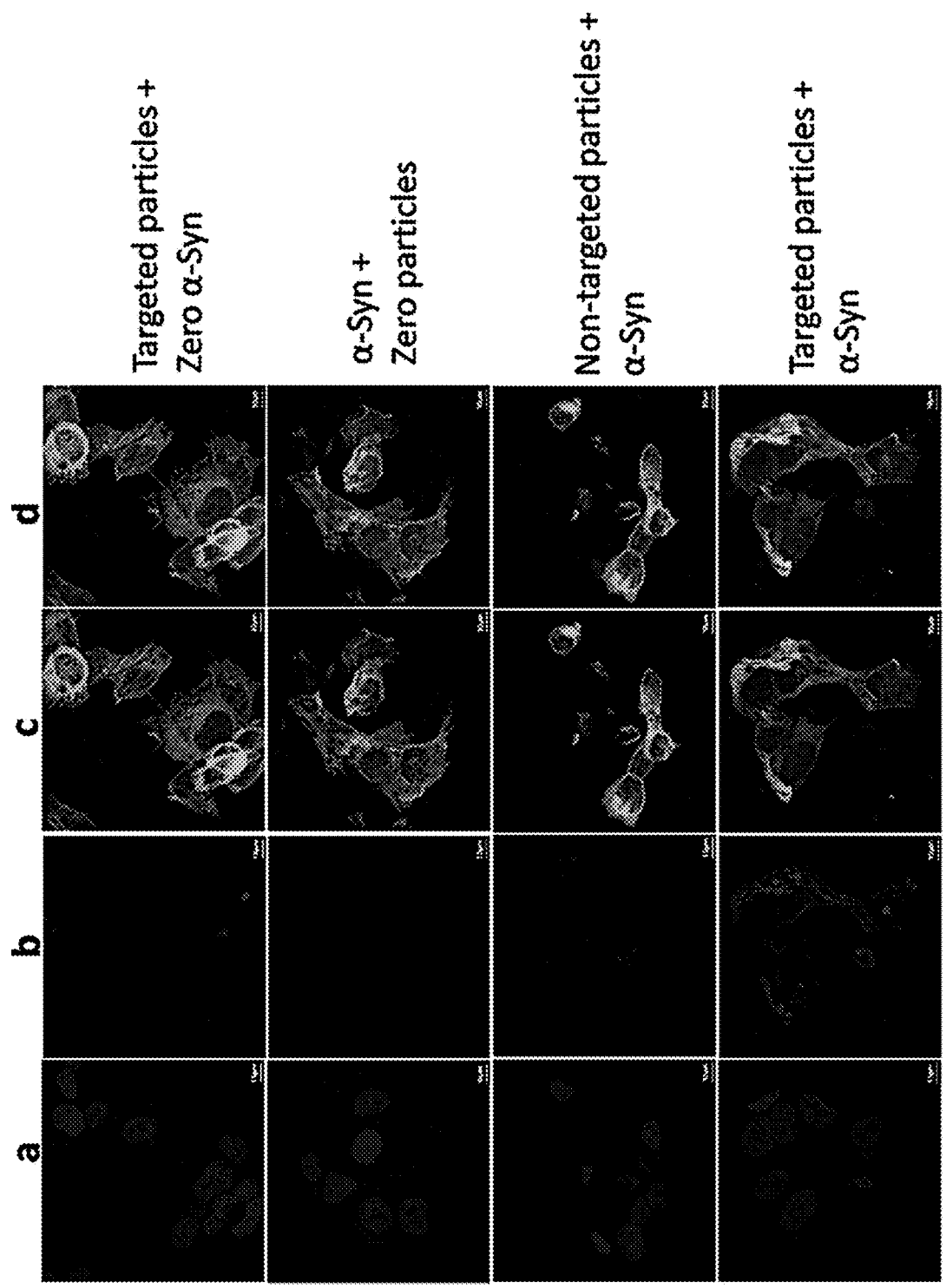
FIG. 23 shows confocal microscopy images of nanoparticle-fibril aggregate uptake within 1.5 hours in SH-SY5Y cells (neuronal cell line) incubated with targeted nanoparticles and fibrils versus controls.
Figure 24:
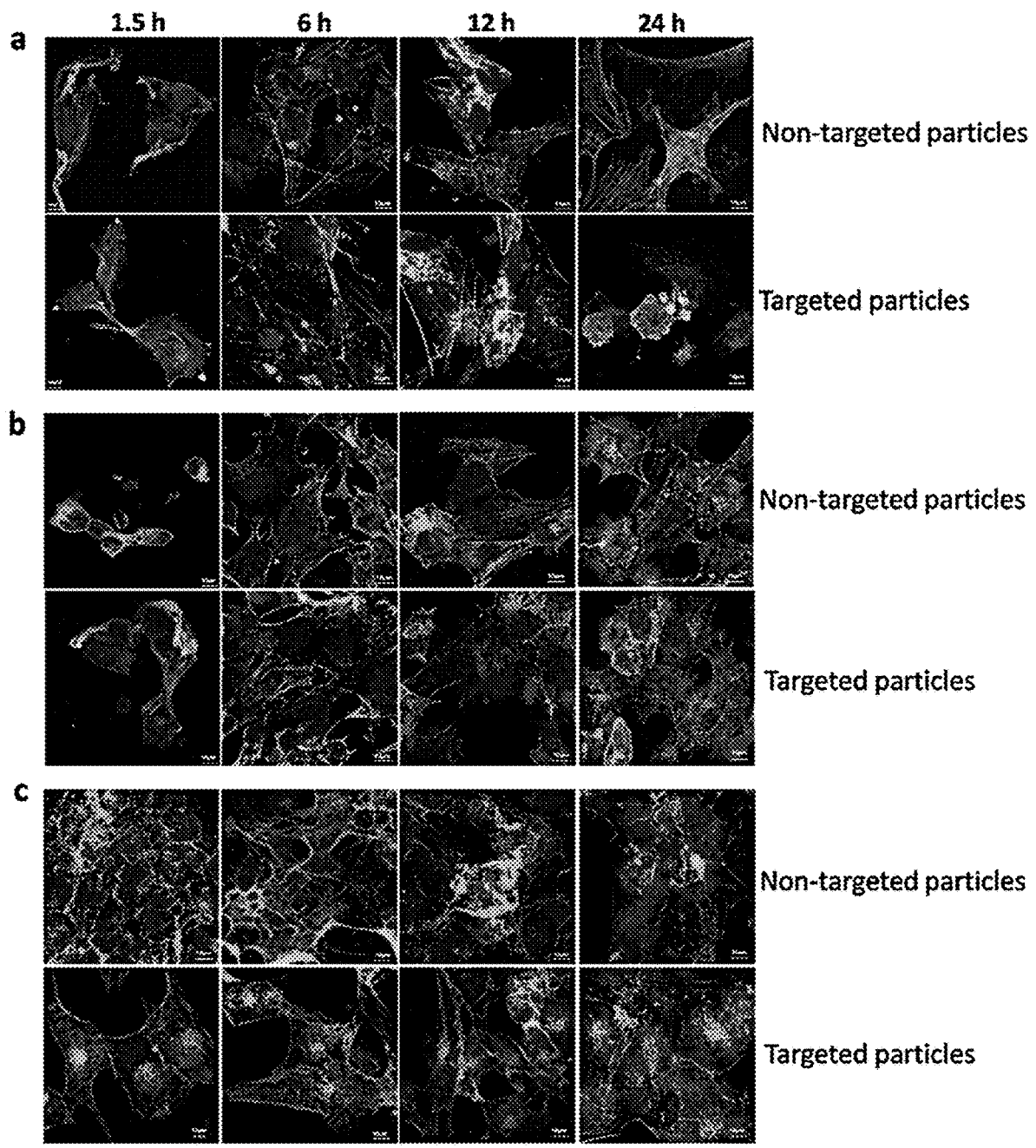
FIG. 24 shows time dependence experiments of nanoparticle-fibril aggregate uptake in three different cell types.

FIG. 23 shows confocal microscopy images of nanoparticle-fibril aggregate uptake within 1.5 hours in SH-SY5Y cells (neuronal cell line) incubated with ligand 8 (XW-01-11) labeled liposome nanoparticles and fibrils versus controls. Column (a) shows a nuclear stain that indicates the presence of cells in all slides; column (b) shows a rhodamine B signal indicative of the location of the nanoparticles and is conspicuous in the slide with cells treated with targeted nanoparticles; column (c) shows a cytoskeleton stain that maps out cell boundaries in all slides; and column (d) shows a composite of all three images, suggesting that the Rhodamine B signal on the test slide is cytosolic, confirming accelerated uptake of nanoparticle-fibril complex.

FIG. 24 shows time dependence experiments of nanoparticle-fibril aggregate uptake in three different cell types. The results show consistent accelerated uptake in cells incubated with the targeted nanoparticles and fibrils compared to cells treated with nontargeted nanoparticles and fibrils. Column (a) shows that HMC-3 cells (microglia cell line) bear significant amounts of cytosolic Rhodamine within the first 6 hours of incubation, which is consistent with aided uptake, compared to cells incubated with nontargeted nanoparticles, which do not show any significant cytosolic Rhodamine B until the 12-hour time point, which is consistent with passive update of liposomal nanoparticles; column (b) shows SH-SY5Y cells (neuronal cell line), which likewise bear significant amounts of cytosolic Rhodamine B within the first 6 hours of incubation, which again is consistent with aided uptake compared to cells incubated with nontargeted nanoparticles, which again do not show any significant cytosolic Rhodamine B until the 12 hour time point; and column (c) shows that T98G cells (astrocyte cell line) bear a similar uptake pattern of targeted particles compared to nontargeted particles as observed in the microglia and neuronal cell lines.

Example 10: In Vitro Toxicity of XW-01-11 Labeled Liposome Nanoparticles

Figure 25:
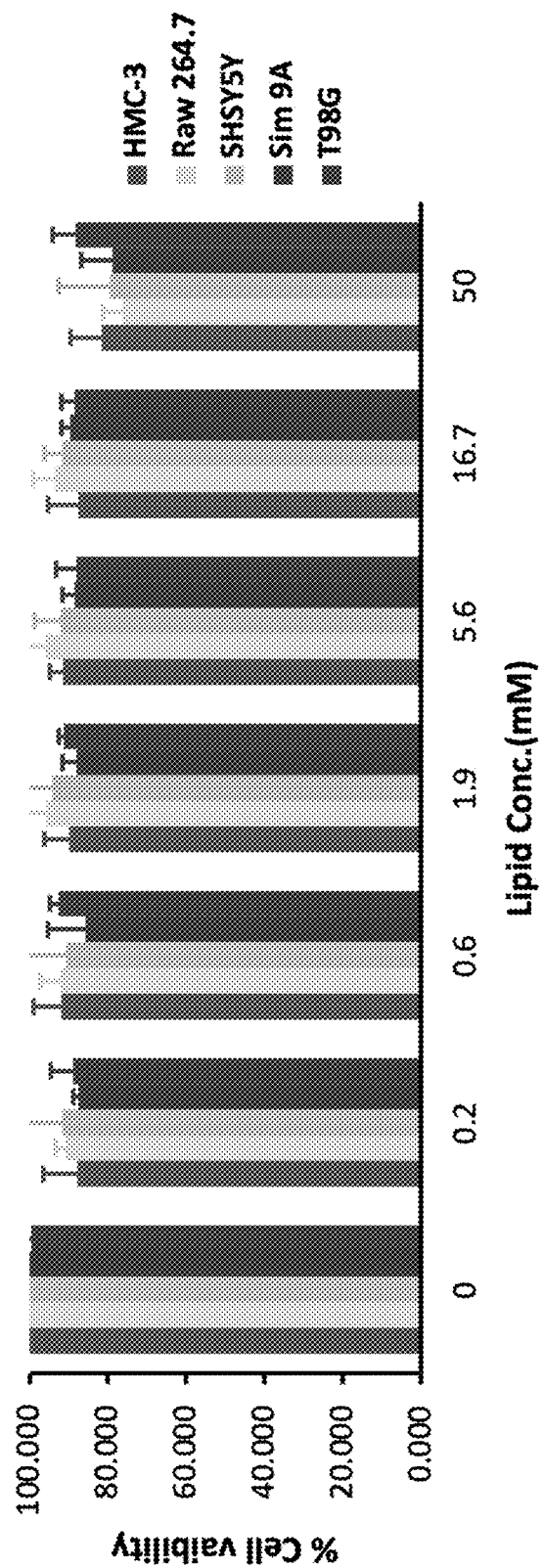
FIG. 25 shows an in vitro cytotoxicity evaluation of α-syn targeted liposomes against different cell types.

In vitro toxicity data was collected from five different cell types. The data suggests that the particles may not pose any serious toxicity concerns at injectable lipid doses (FIG. 25).

Example 11: Contrast Enhanced In Vivo MRI Molecular Imaging of α-Syn in a Mouse Model of PD A solution of the ligand 8 (XW-01-11) labeled liposomes and control liposomes were prepared as described in Example 7 (except without Rhodamine B). MRI was performed on a 1T permanent magnet scanner. Images were acquired using a T1-weighted spin echo (T1w-SE) sequence with the following parameters: SE parameters: TR=600 ms, TE=11.5 ms, slice thickness=1.2 mm, matrix=192×192, FOV=30 mm, slices=16, NEX=4. A53T α-synuclein transgenic line M83 mice (16-18 mos. old, n=6) were pre-scanned, followed by intravenous administration of the ligand 8 (XW-01-11) labeled liposomes (TgT) at a dose of 0.20 mmol Gd/kg of body weight. Delayed scans were performed four days post-contrast administration, after which animals were euthanized and brains harvested for histology analysis. Controls included age-matched wildtype mice (n=6) injected with the ligand 8 (XW-01-11) labeled liposomes (WtT) and transgenic mice (n=6) injected with the non-targeted formulation (TgNT). Brain tissues were histologically assessed with α-syn-4D6 antibody to confirm α-syn pathology.

Figure 26:
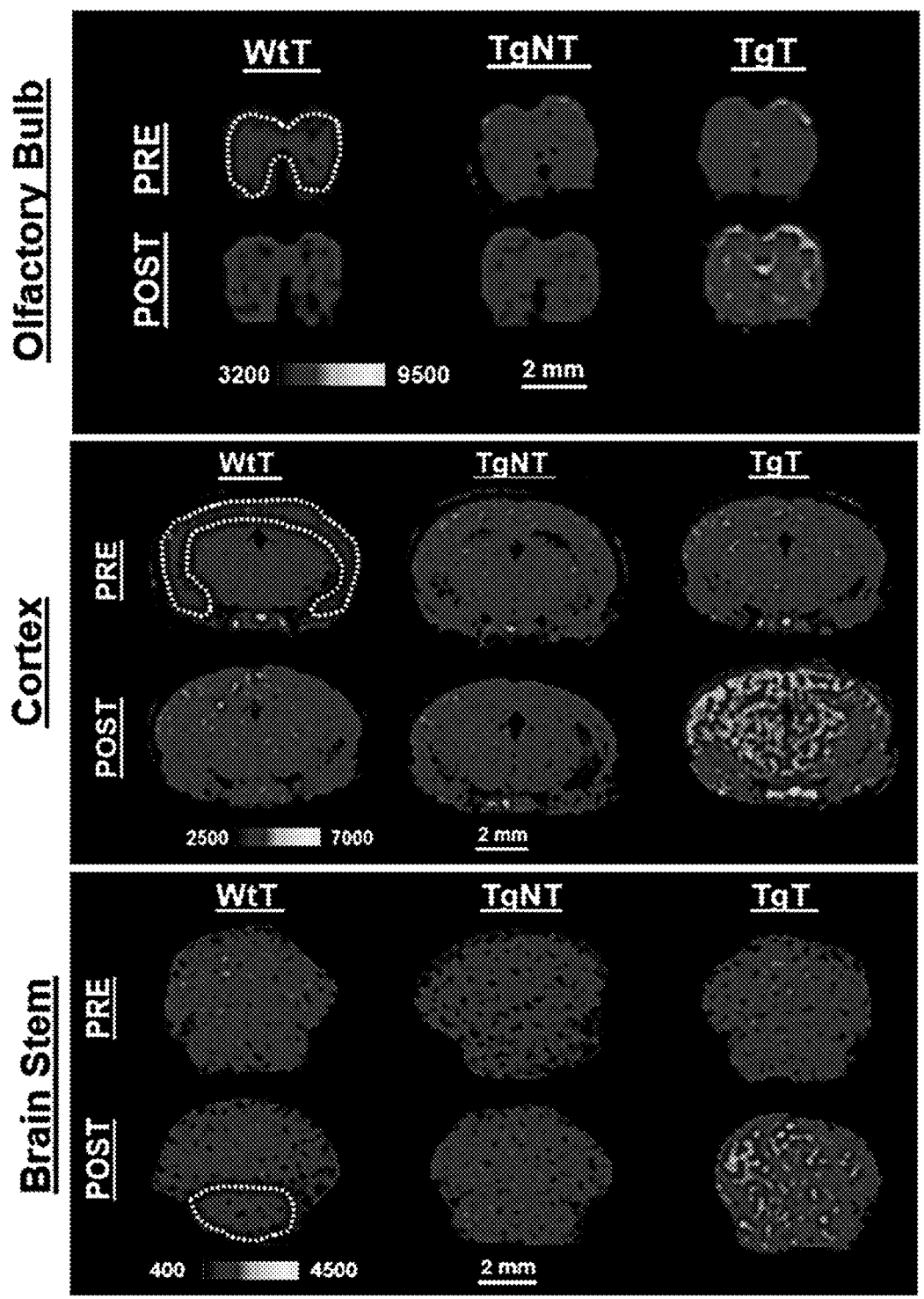
FIG. 26 shows T1-weighted in vivo MR images of the olfactory bulb, cortex, and brain stem of transgenic mice treated with the ligand 8 (XW-01-11) labeled liposome nanoparticles (TgT).
Figure 27:
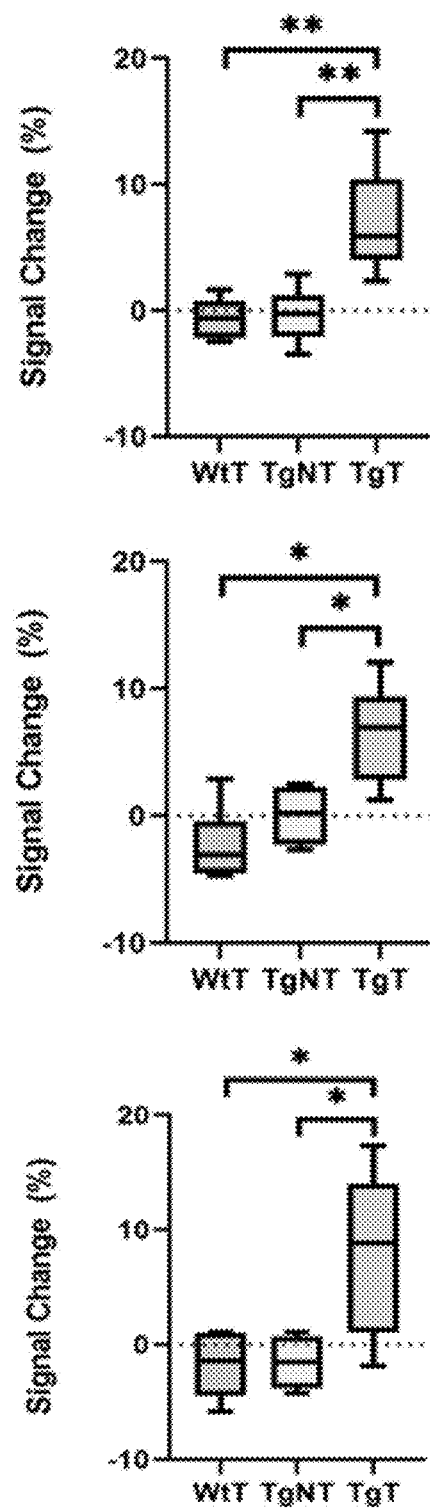
FIG. 27 shows box and whisker plots of change in signal intensity within the demarcated regions of interest, which demonstrate that the change in signal intensity between test and control animals described in FIG. 26 is statistically significant (*$p<0.05\%$ and **$p<0.005\%$).

Post-contrast in vivo MR images showed significant signal enhancement in the transgenic mice treated with the targeted agent compared to controls (FIG. 26). This was attributed to an association between the ligand 8 (XW-01-11) labeled liposomes and α-syn pathology. Signal quantification demonstrated statistically significant differences between test animals versus controls (FIG. 27). Histological analysis (FIG. 28) suggested that the observed differences were consistent with the regional distribution and density of the pathology in this mouse model.

More particularly, FIG. 26 shows T1-weighted in vivo MR images of the olfactory bulb, cortex, and brain stem of transgenic mice treated with the ligand 8 (XW-01-11) labeled liposome nanoparticles (TgT). A significant increase in signal intensity is evident, compared to control age-matched wildtypes treated with the ligand 8 (XW-01-11) labeled liposome nanoparticles (WtT) and transgenics treated with control liposomes (TgT), which show no apparent difference in signal intensity between delayed images and baseline.

FIG. 27 shows box and whisker plots of change in signal intensity within the demarcated regions of interest, which demonstrate that the change in signal intensity between test and control animals described in FIG. 26 is statistically significant (*$p<0.05\%$ and **$p<0.005\%$).

Figure 28:
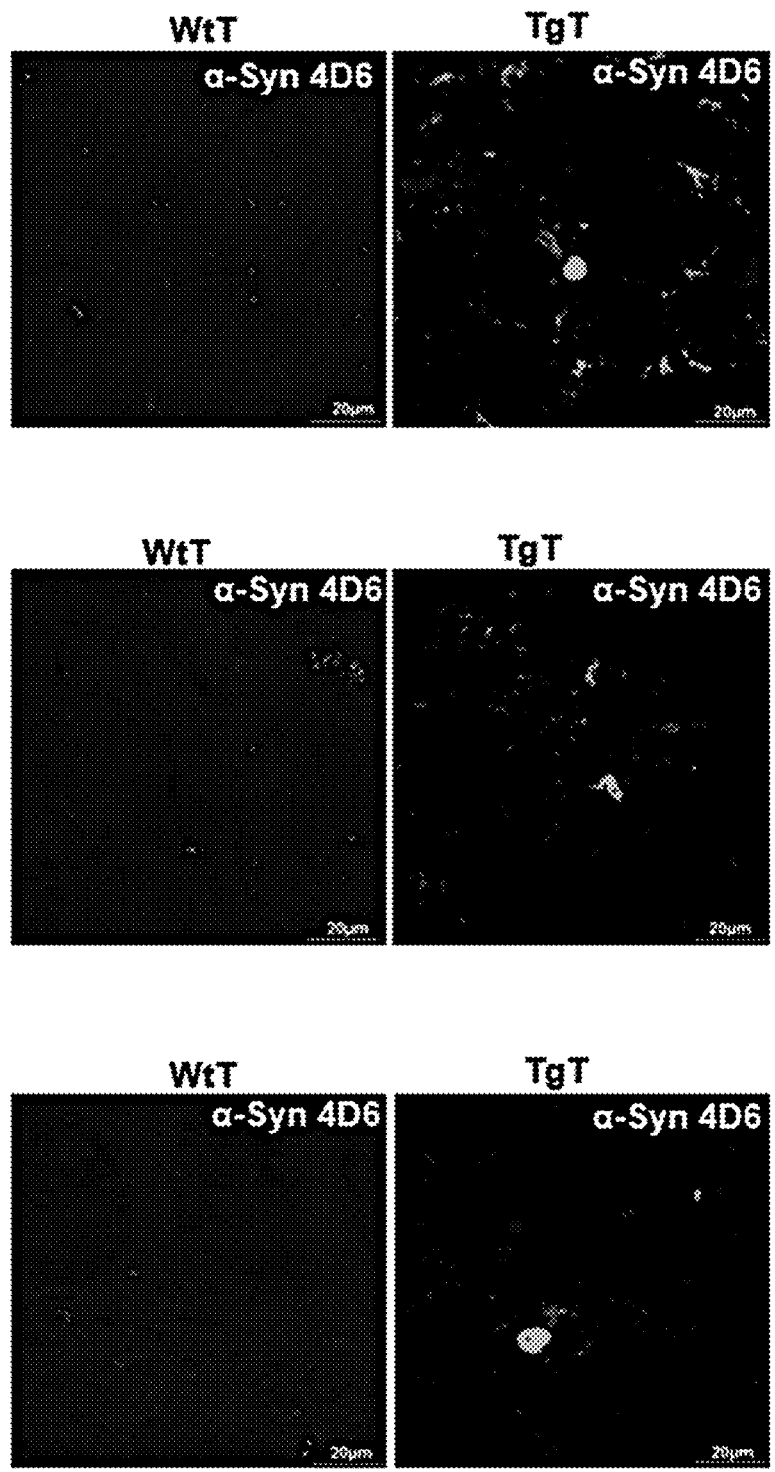
FIG. 28 shows histology analysis as exemplified by anti-mouse α-syn 4D6 antibody labeling of α-syn pathology on brain tissue sections from the WtT and TgT animals described in FIG. 26, which suggests a correlation between delayed MRI signal intensity and α-syn pathology. Scale=20 µm.

FIG. 28 shows histology analysis as exemplified by anti-mouse α-syn 4D6 antibody labeling of α-syn pathology on brain tissue sections from the WtT and TgT animals described in FIG. 26, which suggests a correlation between delayed MRI signal intensity and α-syn pathology. Scale=20 μm.

The in vivo results show that intravenous administration of α-syn targeted liposomes bearing an MRI contrast payload provides an increase in signal intensity consistent with regional distribution of α-syn pathology in the brains of A53T α-synuclein transgenic line M83 mice. Thus, the claimed invention provides a widely accessible tool for early detection of synucleinopathies including PD, LBD, MSA, and PAF.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A liposomal composition, comprising:
a first phospholipid;
an excipient selected from the group consisting of: cholesterol, cholesterol esters, fatty alcohols, fatty acids, and mixtures thereof;
a second phospholipid that is derivatized with a first polymer;
a macrocyclic gadolinium-based imaging agent; and
a third phospholipid that is derivatized with a second polymer, the second polymer being conjugated to a targeting ligand, the targeting ligand being represented by a compound according to Formula I:

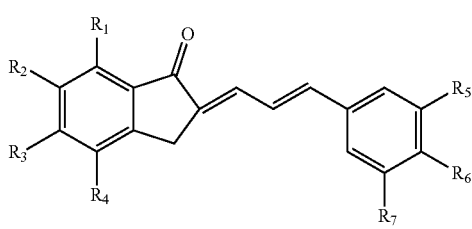

(I)

wherein
$R_1$, $R_2$, $R_3$ and $R_4$ are independently selected from —H, Halogen, —OH, and —Me; and
$R_5$, $R_6$, and $R_7$ are independently selected from —H, —OH, —OMe, —NO$_2$, —NMe$_2$, $C_1$-$C_6$ alkyl, or a substituted or unsubstituted $C_4$-$C_6$ aryl group, or a pharmaceutically acceptable salt thereof.

2. The liposomal composition of claim 1, wherein the first phospholipid comprises hydrogenated soy L-a-phosphatidylcholine ("HSPC").

3. The liposomal composition of claim 1, wherein the second phospholipid that is derivatized with a first polymer comprises 1,2-distearoyl-sn-glycero-3-phosphoethanolamine-N-(methoxy (polyethylene glycol)-2000) ("DSPE-mPEG2000").

4. The liposomal composition of claim 1, wherein the macrocyclic gadolinium-based imaging agent comprises:

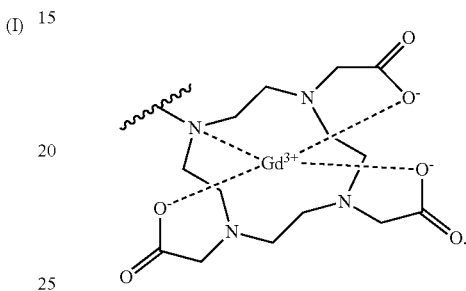

5. The liposomal composition of claim 1, wherein the macrocyclic gadolinium-based imaging agent is conjugated to a fourth phospholipid to comprise:

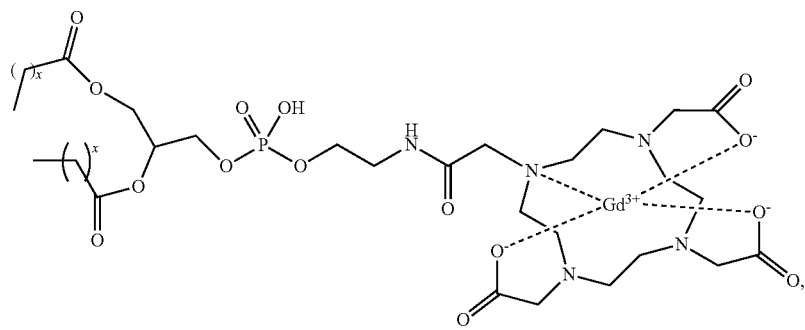

or a salt thereof, and wherein the variable x is one of: 12, 13, 14, 15, 16, 17, or 18.

6. The liposomal composition of claim 5, wherein the variable x is 16 (the conjugate: "Gd(III)-DOTA-DSPE").

7. The liposomal composition of claim 1, wherein the targeting ligand comprises:

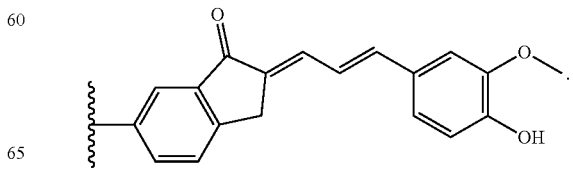

8. The liposomal composition of claim 1, wherein the targeting ligand comprises:

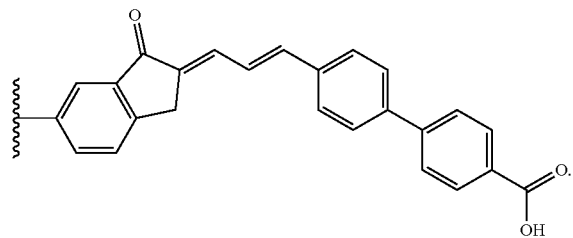 [SMILES: *c1ccc2c(c1)C(=O)/C(=C/C=C/c1ccc(-c3ccc(C(=O)O)cc3)cc1)C2]

9. The liposomal composition of claim 1, wherein the third phospholipid that is derivatized with a second polymer comprises:

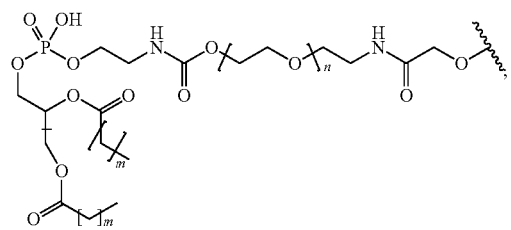

or a salt thereof, wherein the variable n is any integer from about 70 to about 90, and wherein the variable m is one of: 12, 13, 14, 15, 16, 17, or 18.

10. The liposomal composition of claim 1, wherein the conjugate of the third phospholipid, the second polymer, and the targeting ligand comprises:

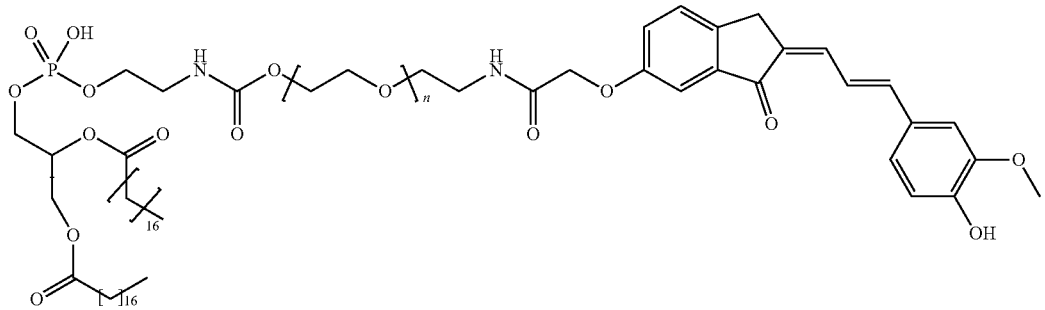

wherein n is 77 or 79.

11. The liposomal composition of claim 1, wherein the conjugate of the third phospholipid, the second polymer, and the targeting ligand comprises:

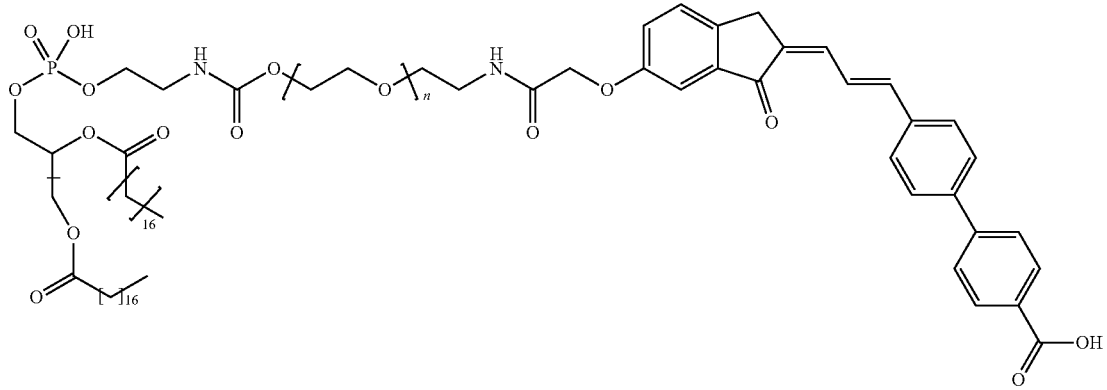

wherein n is 77 or 79.

\* \* \* \* \*